United States Patent
Blumberg et al.

(10) Patent No.: US 9,580,417 B2
(45) Date of Patent: Feb. 28, 2017

(54) PRODRUGS OF HETEROAROMATIC COMPOUNDS

(71) Applicant: Alkermes Pharma Ireland Limited, Dublin (IE)

(72) Inventors: Laura Cook Blumberg, Lincoln, MA (US); Orn Almarsson, Shrewsbury, MA (US)

(73) Assignee: Alkermes Pharma Ireland Limited, Dublin (IE)

( * ) Notice: Subject to any disclaimer, the term of this patent is extended or adjusted under 35 U.S.C. 154(b) by 0 days.

(21) Appl. No.: 14/797,475

(22) Filed: Jul. 13, 2015

(65) Prior Publication Data

US 2016/0009713 A1    Jan. 14, 2016

Related U.S. Application Data

(63) Continuation of application No. 12/978,273, filed on Dec. 23, 2010, now Pat. No. 9,107,911.

(60) Provisional application No. 61/292,998, filed on Jan. 7, 2010.

(51) Int. Cl.
| | | |
|---|---|---|
| *A61K 38/00* | (2006.01) | |
| *C07D 471/04* | (2006.01) | |
| *A61K 31/4192* | (2006.01) | |
| *C07D 403/14* | (2006.01) | |
| *C07K 5/097* | (2006.01) | |

(52) U.S. Cl.
CPC ........ *C07D 471/04* (2013.01); *A61K 31/4192* (2013.01); *C07D 403/14* (2013.01); *C07K 5/0821* (2013.01); *C07K 5/0823* (2013.01)

(58) Field of Classification Search
None
See application file for complete search history.

(56) References Cited

U.S. PATENT DOCUMENTS

| | | | |
|---|---|---|---|
| 9,107,911 B2 * | 8/2015 | Blumberg | .......... A61K 31/4192 |
| 2002/0137739 A1 | 9/2002 | Ohtsuka et al. | |
| 2004/0039027 A1 | 2/2004 | Kamiyama et al. | |
| 2004/0248941 A1 | 12/2004 | Kamiyama et al. | |
| 2006/0293283 A1 | 12/2006 | Kalla et al. | |

FOREIGN PATENT DOCUMENTS

| | | |
|---|---|---|
| WO | 2006079610 A1 | 8/2006 |
| WO | 2008012852 A1 | 1/2008 |

OTHER PUBLICATIONS

Hasan, A., et al., "Synthesis and Biological Studies of Unsaturated Acyclonucleoside Analogues of S-Adenosyl-L-Homocysteine Hydrolase Inhibitors," J. Med. Chem., 35, pp. 1435-1439 (1992).

Mishra, A., et al., "Studies in Nucleosides: Part XVI—Synthesis of Azathioprine Analogues," Indian Journal of Chemistry, vol. 26B, pp. 847-850 (1987).

Colombo, R., et al., "Acid-Labile Histidine Side-Chain Protection: The N(.pi.)-t-Butoxymethyl Group," Journal of The Chemical Society, Chemical Communications, No. 5, p. 292 (1984).

* cited by examiner

*Primary Examiner* — Jeanette Lieb
(74) *Attorney, Agent, or Firm* — Elmore Patent Law Group, P.C.; Carolyn S. Elmore; Edgar W. Harlan

(57) ABSTRACT

The present invention relates to prodrugs of parent drug compounds containing heteroaromatic NH groups.

16 Claims, No Drawings

PRODRUGS OF HETEROAROMATIC COMPOUNDS

RELATED APPLICATIONS

This application is a continuation of U.S. application Ser. No. 12/978,273, filed Dec. 23, 2010, which claims the benefit of U.S. Provisional Application No. 61/292,998, filed on Jan. 7, 2010. The entire teachings of the above applications are incorporated herein by reference.

BACKGROUND OF THE INVENTION (i) Field of the Invention

The present invention relates to prodrugs of heteroaromatic drugs.

(ii) Background of the Invention

Drug delivery systems are often critical for the safe and effective administration of a biologically active agent. Perhaps the importance of these systems is best realized when patient compliance and consistent dosing are taken under consideration. For instance, reducing the dosing requirement for a drug from four-times-a-day to a single dose per day would have significant value in terms of ensuring patient compliance and optimizing therapy.

Optimization of a drug's bioavailability and duration of action has many potential benefits. For patient convenience and enhanced compliance it is generally recognized that less frequent dosing is desirable. By extending the period through which the drug is released, a longer duration of action per dose is expected. This will then lead to an overall improvement of dosing parameters such as taking a drug once a day where it has previously required four doses per day or dosing once a week or even less frequently when daily dosing was previously required. Many drugs are presently dosed once per day, but not all of these drugs have pharmacokinetic properties that are suitable for dosing intervals of exactly twenty-four hours. Extending the period through which these drugs are released would also be beneficial.

One of the fundamental considerations in drug therapy involves the relationship between blood levels and therapeutic activity. For most drugs, it is of primary importance that serum levels remain between a minimally effective concentration and a potentially toxic level. In pharmacokinetic terms, the peaks and troughs of a drug's blood levels ideally fit well within the therapeutic window of serum concentrations. For certain therapeutic agents, this window is so narrow that dosage formulation becomes critical.

In an attempt to address the need for improved bioavailability, several drug release modulation technologies have been developed. Enteric coatings have been used as a protector of pharmaceuticals in the stomach and microencapsulating active agents using proteinaceous microspheres, liposomes or polysaccharides have been effective in abating enzymatic degradation of the active agent. Enzyme inhibiting adjuvants have also been used to prevent enzymatic degradation.

A wide range of pharmaceutical formulations provide sustained release through microencapsulation of the active agent in amides of dicarboxylic acids, modified amino acids or thermally condensed amino acids. Slow release rendering additives can also be intermixed with a large array of active agents in tablet formulations.

While microencapsulation and enteric coating technologies impart enhanced stability and time-release properties to active agent substances these technologies suffer from several shortcomings. Incorporation of the active agent is often dependent on diffusion into the microencapsulating matrix, which may not be quantitative and may complicate dosage reproducibility. In addition, encapsulated drugs rely on diffusion out of the matrix or degradation of the matrix, or both, which is highly dependent on the chemical properties and water solubility of the active agent. Conversely, water-soluble microspheres swell by an infinite degree and, unfortunately, may release the active agent in bursts (dose dumping) with potential for adverse effects and limited active agent available for sustained release. Furthermore, in some technologies, control of the degradation process required for active agent release is unreliable. For example, because an enterically coated active agent depends on pH to release the active agent and pH and residence time varies, the release rate and timing is difficult to control.

Several implantable drug delivery systems have utilized polypeptide attachment to drugs. Additionally, other large polymeric carriers incorporating drugs into their matrices are used as implants for the gradual release of drug. Yet another technology combines the advantages of covalent drug attachment with liposome formation where the active ingredient is attached to highly ordered lipid films.

However there is still a need for an active agent delivery system that is able to deliver certain active agents which have been heretofore not formulated or difficult to formulate in a sustained release formulation for release over a sustained period of time and which is convenient for patient dosing.

There is a generally recognized need for sustained delivery of drugs that reduces the daily dosing requirement and allows for controlled and sustained release of the parent drug and also avoids irregularities of release and cumbersome formulations encountered with typical dissolution controlled sustained release methods.

SUMMARY OF THE INVENTION

The present invention accomplishes this by extending the period during which a heteroaryl NH-containing parent drug is released and absorbed after administration to the patient and providing a longer duration of action per dose than is currently expected. In one embodiment, the compounds suitable for use in the methods of the invention are derivatives of heteroaryl NH-containing parent drugs that are substituted at the NH nitrogen atom with labile prodrug moieties. Preferably, the prodrug moieties are hydrophobic and reduce the solubility at physiological pH (pH 7.0), as well as modulate polarity and lipophilicity parameters of the prodrug as compared to the parent drug. In preferred embodiments, the prodrug moieties reduce the solubility of prodrug as compared to the parent drug in a pH range from about 1.2 to about 7.5, from about 3 to about 7.5, from about 4 to about 7.5, or from about 5 to about 7.5.

In one embodiment, the invention provides a prodrug compound of Formula I

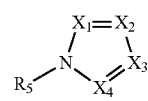

I or a pharmaceutically acceptable salt thereof, wherein each of $X_1$ to $X_4$ is independently N or CR, provided that at least one of $X_1$-$X_4$ is CR. The R groups combine to form the portion of the prodrug compound in addition to the five-membered heteroaromatic ring. For example, the R groups can be independently hydrogen, optionally substituted aliphatic, aromatic, heteroaromatic or a combination thereof. The R groups can also be taken together with the carbon atoms to which they are attached to form one or more optionally substituted fused ring systems. $R_5$ is selected from —$C(R_8)(R_9)$—$OR_{10}$, —$C(R_8)(R_9)$—$OC(O)OR_{10}$, —$C(R_8)(R_9)$—$OC(O)R_{10}$, —$C(R_8)(R_9)$—$OC(O)NR_{11}R_{12}$, —$C(R_8)(R_9)$—$OPO_3MY$, —$C(R_8)(R_9)$—$OP(O)(OR_{11})(OR_{12})$, —$C(R_8)(R_9)$—$OP(O)_2(OR_{11})M$, —$[C(R_8)(R_9)O]_n$—$R_{10}$, —$[C(R_8)(R_9)O]_n$—$C(O)OR_{10}$, —$[C(R_8)(R_9)O]_n$—$C(O)R_{10}$, —$[C(R_8)(R_9)O]_n$—$C(O)NR_{11}R_{12}$, —$[C(R_8)(R_9)O]_n$—$OPO_3MY$, —$[C(R_8)(R_9)O]_n$—$P(O)_2(OR_{11})M$ and —$[C(R_8)(R_9)O]_n$—$P(O)(OR_{11})(OR_{12})$. $R_8$ and $R_9$ are each independently hydrogen, aliphatic or substituted aliphatic.

In an embodiment, $R_{10}$, or least one of $R_{11}$ and $R_{12}$, is an aliphatic, aryl or substituted aryl group that reduces the solubility of the prodrug under physiological conditions compared to the parent drug.

In an embodiment, $R_{10}$ is $C_1$-$C_{24}$-alkyl, substituted $C_1$-$C_{24}$-alkyl, $C_2$-$C_{24}$-alkenyl, substituted $C_2$-$C_{24}$-alkenyl, $C_2$-$C_{24}$-alkynyl, substituted $C_2$-$C_{24}$-alkenyl, $C_3$-$C_{12}$-cycloalkyl, substituted $C_3$-$C_{12}$-cycloalkyl, aryl or substituted aryl.

In an embodiment, $R_{11}$ and $R_{12}$ are each independently hydrogen, aliphatic or substituted aliphatic, provided that at least one of $R_{11}$ and $R_{12}$ is $C_1$-$C_{24}$-alkyl, substituted $C_1$-$C_{24}$-alkyl, $C_2$-$C_{24}$-alkenyl, substituted $C_2$-$C_{24}$-alkenyl, $C_2$-$C_{24}$-alkynyl, substituted $C_2$-$C_{24}$-alkenyl, $C_3$-$C_{24}$ cycloalkyl, substituted $C_3$-$C_{12}$-cycloalkyl; or $R_{11}$ and $R_{12}$ together form a substituted or unsubstituted alkylene or alkenylene group which can optionally be interrupted by up to three heteroatoms independently selected from oxygen, nitrogen and sulfur.

Y and M are the same or different and each is a monovalent cation; or M and Y together are a divalent cation; and n is 2 or 3.

In another embodiment, the invention provides a method of sustained delivery of a heteroaryl NH-containing parent drug comprising administering to a subject an effective amount of a prodrug compound produced by substituting a labile, hydrophobic aldehyde-linked prodrug moiety on the heteroaromatic NH nitrogen atom. Preferably the prodrug compound has decreased solubility under physiological conditions and sustained activity upon dosing compared to the parent drug compound. In one embodiment, the heteroaryl NH-containing parent drug is represented by Formula II:

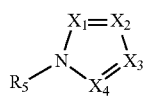

II where $X_1$ to $X_4$ are as previously defined. In this embodiment the prodrug is represented by Formula I:

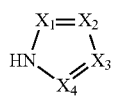

I as defined previously.

The invention also provides a method of administering a heteroaryl NH-containing parent drug comprising administering to a subject an effective amount of a prodrug compound produced by substituting a labile, hydrophobic aldehyde-linked prodrug moiety on the heteroaromatic NH nitrogen atom. The method substantially eliminates undesirable side effects seen upon administration of the parent drug itself by lowering the maximum plasma concentration of the patrent drug while maintaining sustained therapeutic levels. In certain embodiments, the side effect of the parent drug is sedation. In a preferred embodiment, the prodrug compound is of Formula I and the parent drug is of Formula II.

In another embodiment, the invention provides a method of producing a prodrug of a parent heteroaromatic NH-containing drug compound, wherein the prodrug has decreased solubility under physiological conditions and sustained activity upon dosing compared to the parent drug compound. The method comprises modifying the parent drug by substituting a labile, hydrophobic prodrug moiety on the heteroaromatic NH nitrogen atom. Preferably, the parent drug compound is represented by Formula II, the prodrug moiety is represented by $R_5$, where $R_5$ has the meaning given above, and the prodrug is represented by Formula I.

The invention also provides pharmaceutical compositions comprising a compound of Formula I and methods of using a compound of Formula I in therapy.

DETAILED DESCRIPTION OF THE INVENTION

The prodrug compounds of the present invention provide sustained or extended therapeutic levels of the parent compound following administration. "Sustained release" typically refers to shifting absorption toward slow first-order kinetics. "Extended release" typically refers to providing zero-order kinetics to the absorption of the compound. The mechanism for timed release may be due to several factors including, but not limited to, the decreased solubility of the prodrug relative to the parent drug, resulting in more gradual dissolution and slower release of the parent drug by the action of serum enzymes or chemical hydrolysis. The term "sustained release" as used herein means that administration of a prodrug of the invention results in effective systemic, local or plasma levels of the parent drug in the of the patient for a period of time that is longer that resulting from administration of the parent drug itself.

The heteroaromatic NH-containing drug can be any heteroaromatic NH-containing drug that induces a desired local or systemic effect. Such drugs comprise a heteroaromatic ring comprising an NH group, such as five-membered nitrogen-containing heteroaromatic groups or fused polycyclic groups comprising a five-membered nitrogen-containing heteroaromatic group. Preferably the heteroaromatric group has a pKa, as measured in dimethylsulfoxide, of about 21 or less.

Heteroaromatic NH-containing drug drugs include broad classes of compounds. In general, this includes: analgesic agents; anesthetic agents; antiarthritic agents; respiratory drugs, including antiasthmatic agents; anticancer agents, including antineoplastic agents; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, CNS agents; beta-blockers and antiarrhythmic agents; central nervous system stimulants; nootropics; cough and cold preparations, including decongestants; diuretics; genetic materials; herbal remedies; hormonolytics; hypnotics; hypoglycemic agents; immunosuppressive agents; leukotriene inhibitors; mitotic inhibitors; muscle relaxants; narcotic antagonists; opioid agonists; nicotine; nutritional agents, such as vitamins, essential amino acids and fatty acids; ophthalmic drugs such as antiglaucoma agents; parasympatholytics; peptide drugs; psychostimulants; sedatives; steroids; sympathomimetics; tranquilizers; and vasodilators including general coronary, peripheral and cerebral.

Specific heteroaromatic NH-containing parent drugs represent a variety of drug classes. Such drugs include tranquilizers and sedatives, such as mepiprazole and dexmedetomidine; anthelmintic agents, such as albendazole, carbendazole, cyclobendazole, mebendazole and thiabendazole; antimigraine agents, such as almotriptan, dolasetron, eletriptan, lisuride, naratriptan, rizatriptan, sumatriptan, frovatriptan, zolmitriptan and ergotamine; treatments for irritable bowel syndrome, such as alosetron; antiviral agents, such as delavirdine and atevirdine; antihypertensive agents, such as bopindolol, bucindolol, candesartan, deserpidine, mibefradil, ergoloid mesylate, indoramin, irbesartan, mepindolol, olmesartan, reserpine, rescinnamine, losartan, tasosartan, valsartan, raubasine, syrosingopine, carmoxirole and rescimetol; anti-Parkinson agents, such as cabergoline, pergolide, bromocriptine and terguride; bronchodilators, such as ambuphylline; antiulcerative agents, such as cimetidine, lansoprazole, omeprazole, pantaprozole and rabeprazole; antibacterial agents, such as cefatrizine and daptomycin; oxytocic agents, such as ergonovine and methylergonovine; analgesics, such as etodolac; antineoplastic agents, such as liarozole, pemetrexed, thiamiprine, vinblastine, vincristine, vindesine, vinorelbine, voacamine and venflunine; antidepressants, such as oxypertine, indalpine and roxindole; antiallergic agents, such as pemirolast, tazanolast and traxanox; cardiotonic agents, such as pimobendan and sulmazole; antiasthmatics, such as pranlukast; antiemetics, such as ramosetron, tropisetron and alizapride; vasodilators, such as bendazole and tadalafil; anti-gout agents, such as allopurinol; antirheumatic agents, such as azathioprine; mydriatics, such as yohimbine; therapies for congestive heart failure, such as conivaptan; and hormonal agents, such as adrenoglomerulotropin, octreotide, somatostatin, exenatide, teriparatide, leuprorelin and goserelin.

In one embodiment, the parent drug is a peptide comprising at least one heteroaromatic NH group. Such peptides include peptides comprising from 2 to about 50, from 2 to about 40, from 2 to about 20 or from 2 to about 12 amino acid residues, including at least one residue selected from tryptophan and histidine. Suitable peptides include, but are not limited to, thyrotropin releasing hormone (TRH), exenatide, daptomycin, octreotide, somatostatin, teriparatide, leuprorelin and goserelin.

While the heteroaromatic NH-containing parent drugs from which the prodrugs of the invention may be derived are numerous, many of the chemical structures of the prodrugs of the invention can be characterized by certain general structure types. One type includes compounds wherein the heteroaromatic group is a pyrrole group. Another type includes compounds wherein the heteroaromatic group is an imidazole group. Another type includes compounds wherein the heteroaromatic group is a 1,2,3- or 1,2,4-triazole group. Another type includes compounds wherein the heteroaromatic group is a tetrazole group. Another type includes compounds wherein the heteroaromatic group is a benzimidazole group. Another type includes compounds wherein the heteroaromatic group is an indole group. Another type includes compounds wherein the heteroaromatic group is a pyrazole group.

Benzimidazole-containing parent drugs which can be modified to produce prodrugs of the invention include albenazole, carbendazole, cyclobendazole, lansoprazole, liarozole, mebendazole, mizolastine, omeprazole, pantaprazole, pimobendan, rabeprazole, thiabendazole, bendazol and mibepradil. Preferred benzimidazole-containing drugs include lansoprazole, mibefradil and pimobendan.

Imidazole-containing parent drugs which can be modified to produce prodrugs of the invention include alosetron, ambuphylline, cimetidine, conivaptan, dexmedetomidine, ramosetron, thiamiprine, sulmazole, azathioprine, exenatide, teriparatide, thyrotropin releasing hormone (TRH), goserelin and leuprorelin. Preferred imidazole-containing drugs include conivaptan, sulmazole and azathioprine.

Indole-containing parent drugs which can be modified to produce prodrugs of the invention include almotriptan, atevirdine, bopindolol, bromocriptine, bucindolol, cabergoline, delavirdine, deserpidine, dolasetron, eletriptan, ergoloid mesylate, ergonovine, etodolac, frovatriptan, indoramin, lisuride, mepidolol, methylergonovine, naratriptan, oxypertine, pemetrexed, pergolide, rescinnamine, reserpine, rizatriptan, sumatriptan, tadalafil, tropisetron, adrenoglomerulotriptan, bromocriptine, ergotamine, indalpine, raubasine, reserpiline, roxindole, syrosingopine, terguride, vinblastine, vincristine, vindesine, vinorelbine, voacamine, vinflunineatevirdine, carmoxirole, rescimetol, yohimbine, zolmitriptan, octreotide, somatostatin, exenatide, teriparatide, daptomycin, leuprorelin and goserelin. Preferred indole-containing drugs include bopindolol, bucindolol, cabergoline, dolasetron, indoramin, oxypertine, pergolide, rescinnamine, reserpine, atevirdine, carmoxirole and rescimetol.

Pyrazole-containing parent drugs which can be modified to produce prodrugs of the invention include mepiprazole and allopurinol.

Tetrazole-containing parent drugs which can be modified to produce prodrugs of the invention include candesartan, irbesartan, losartan, olmesartan, pemirolast, pranlukast, tasosartan, traxanox and valsartan.

Triazole-containing parent drugs which can be modified to produce prodrugs of the invention include cefatrizine and alizapride.

Particularly preferred parent drugs which can be modified according to the invention include bopindolol, bucindolol, cabergoline, candesartan, cefatrizine, conivaptan, indoramin, irbesartan, lansoprazole, mibefradil, olmesartan, oxypertine, pemirolast, pergolide, pimobendan, rescinnamine, reserpine, valsartan, sulmazole, azathioprine, atevirdine, carmoxirole and rescimetol.

It is to be understood that any of the parent drugs or prodrugs of the invention may be further substituted as that term is defined herein so long as the substituted parent drug or parent prodrug, which when administered to a patient in vivo, becomes cleaved by chemical and/or enzymatic hydrolysis thereby releasing the parent drug moiety such that a sufficient amount of the compound intended to be delivered to the patient is available for its intended therapeutic use in a sustained release manner. One example of a substituted parent drug or a prodrug comprising a parent drug is a pharmaceutically acceptable ester of the parent drug. A parent drug or parent prodrug may be further substituted for any purpose including, but not limited to, stabilization of the parent during synthesis of the prodrug and stabilization of the prodrug for administration to the patient.

In one embodiment, the parent drug is represented by one of Formulas III-VIII,

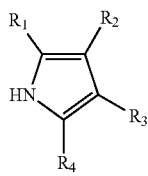

III

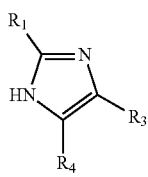

IV

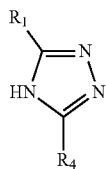

V

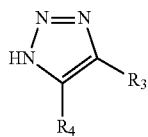

VI

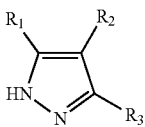

VII

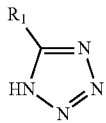

VIII where $R_1$, $R_2$, $R_3$ and $R_4$ together form the portion of the parent drug in addition to the five-membered heteroaromatic ring. For example, each $R_1$, $R_2$, $R_3$ and $R_4$ can be independently hydrogen, optionally substituted aliphatic, aromatic, heteroaromatic or a combination thereof. Any two of $R_1$-$R_4$ can also be taken together with the carbon atoms to which they are attached to form one or more optionally substituted fused ring systems. In one embodiment, $R_1$, $R_2$, $R_3$ and $R_4$ are each independently selected from hydrogen, halogen, amino, substituted amino, optionally substituted aliphatic, optionally substituted aryl and optionally substituted heterocyclyl; or $R_1$ and $R_2$, $R_2$ and $R_3$, or $R_3$ and $R_4$, together with the carbon atoms to which they are attached, form an optionally substituted cycloalkenyl, aryl, heterocyclyl or heteroaryl ring.

In one embodiment, the parent drug is represented by Formula IX,

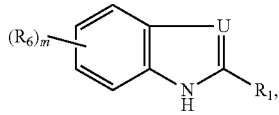

IX where U is $C(R_2)$ or N; $R_1$ and $R_2$ have the identities given above; each $R_6$ is independently optionally substituted aliphatic, aromatic, heteroaromatic or a combination thereof. Any two of $R_6$, $R_1$ and $R_2$ can also be taken together with the carbon atoms to which they are attached to form one or more optionally substituted fused ring systems. In one embodiment, each $R_6$ is independently selected from hydrogen, halogen, amino, substituted amino, optionally substituted aliphatic, optionally substituted aryl and optionally substituted heterocyclyl; or two adjacent $R_6$ groups, together with the carbon atoms to which they are attached, form an optionally substituted cycloalkenyl, aryl, heterocyclyl or heteroaryl ring; and m is an integer from 0 to 4.

In an embodiment, the prodrug compound of the invention is represented by one of Formulas X to XV:

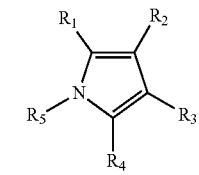

X

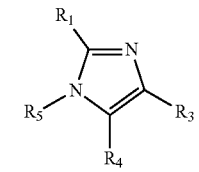

XI

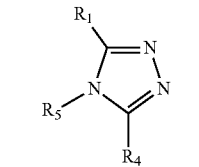

XII

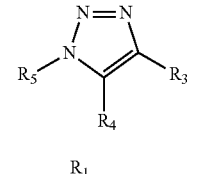

XIII

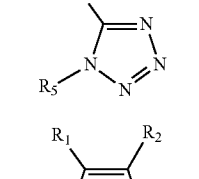

XIV

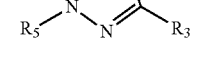

XV where $R_1$, $R_2$, $R_3$, $R_4$ and $R_5$ are as previously defined. $R_5$ is preferably selected from —CH($R_8$)—OR$_{10}$, —CH($R_8$)—

OC(O)OR$_{10}$, —CH(R$_8$)—OC(O)R$_{10}$, —CH(R$_8$)—OC(O)NR$_{11}$R$_{12}$, —CH(R$_8$))—OPO$_3$MY, —CH(R$_8$)—OP(O)$_2$(OR$_{11}$)M, —CH(R$_8$)—OP(O)(OR$_{11}$)(OR$_{12}$), —[CH(R$_8$)O]$_n$—R$_{10}$, —[CH(R$_8$)O]$_n$—C(O)OR$_{10}$, —[CH(R$_8$)O]$_n$—C(O)R$_{10}$, —[CH(R$_8$)O]$_n$—C(O)NR$_{11}$R$_{12}$, —[CH(R$_8$)O]$_n$—PO$_3$MY, —[CH(R$_8$)O]$_n$—P(O)$_2$(OR$_{11}$)M and —[CH(R$_8$)O]$_n$—P(O)(OR$_{11}$)(OR$_{12}$); R$_8$ is hydrogen, aliphatic or substituted aliphatic; R$_{10}$ is C$_1$-C$_{24}$-alkyl, substituted C$_1$-C$_{24}$-alkyl, C$_2$-C$_{24}$-alkenyl, substituted C$_2$-C$_{24}$-alkenyl, C$_2$-C$_{24}$-alkynyl, substituted C$_2$-C$_{24}$-alkynyl, C$_3$-C$_{12}$ cycloalkyl, substituted C$_3$-C$_{12}$-cycloalkyl, aryl or substituted aryl; R$_{11}$ and R$_{12}$ are each independently hydrogen, aliphatic, substituted aliphatic, aryl or substituted aryl, provided that at least one of R$_{11}$ and R$_{12}$ is not hydrogen; or R$_{11}$ and R$_{12}$ together form a substituted or unsubstituted alkylene or alkenylene group which can optionally be interrupted by up to three heteroatoms independently selected from oxygen, nitrogen and sulfur; Y and M are the same or different and each is a monovalent cation; or M and Y together are a divalent cation; and n is 2 or 3; or a pharmaceutically acceptable salt thereof.

In one embodiment, the prodrug compounds of the invention are represented by Formula XVI,

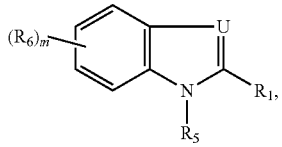

XVI where U, R$_1$, R$_5$, R$_6$ and m each have the identities given above.

In a preferred embodiment of the compounds of the invention, R$_9$ is hydrogen and R$_8$ is hydrogen; C$_1$-C$_3$-alkyl, preferably methyl or isopropyl; —C(O)H, —CH(OH)CH$_2$OH, —C(O)OH or —C(O)OEt. In a particularly preferred embodiment, both R$_8$ and R$_9$ are hydrogen.

In an embodiment of the compounds of the invention, R$_5$ is selected from —CH(R$_8$)—OC(O)OR$_{10}$, —CH(R$_8$)—OC(O)R$_{10}$ and —CH(R$_8$)—OC(O)NR$_{11}$R$_{12}$. In another embodiment, R$_5$ is selected from —CH(R$_8$)—OPO$_3$MY, —CH(R$_8$)—OP(O)$_2$(OR$_{11}$)M and —CH(R$_8$)—OP(O)(OR$_{11}$)(OR$_{12}$).

In an embodiment of the compounds of the invention, R$_{10}$, or at least one of R$_{11}$ and R$_{12}$, is optionally substituted aryl, C$_7$-C$_{24}$-alkyl, C$_7$-C$_{24}$-alkenyl, or C$_7$-C$_{24}$-alkynyl. In another embodiment, R$_{10}$, or at least one of R$_{11}$ and R$_{12}$, is branched C$_3$-C$_{24}$-alkyl, -alkenyl or -alkynyl, preferably branched C$_7$-C$_{24}$ alkyl, -alkenyl or -alkynyl. In one embodiment, R$_{10}$, or at least one of R$_{11}$ and R$_{12}$, is a secondary or tertiary C$_3$-C$_{24}$- or C$_7$-C$_{24}$-alkyl, -alkenyl or -alkynyl group, such as C$_3$-C$_{12}$-cycloalkyl, 1-methyl-C$_3$-C$_{12}$-cycloalkyl, isopropyl, sec-butyl, t-butyl, pent-2-yl, hex-2-yl, hept-2-yl, cyclopentyl, neopentyl, 3-methylpent-3-yl, 3-ethylpent-3-yl; 2,3-dimethylbut-2-yl; 1-methylcyclopentyl, 1-methylcyclohexyl, 1-ethylcyclohexyl or a branched alkyl group corresponding to one of formulas (i)-(v) below.

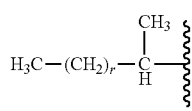

(i)

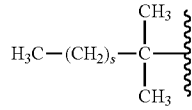

(ii)

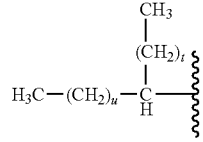

(iii)

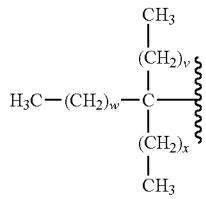

(iv)

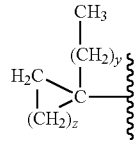

(v)

In these groups, r is 0 to 21 and s is 0 to 20. Each of t and u is independently 0 to 21, provided that the sum of t and u is from 0 to 21. Each of v, w and x is independently 0 to 20, provided that the sum of v, w and x is from 0 to 20. z is an integer from 1 to 10 and y is an integer from 0 to 20, provided that the sum of z and y is from 1 to 21. Preferably, r is an integer from 5 to 21; s is an integer from 1 to 20; the sum of t and u is from 5 to 21; the sum of v, w and x is from 4 to 20; and the sum of y and z is from 5 to 21. R$_{10}$ can also be an alkenyl or alkynyl group derived from one of the alkyl groups of formulas i to v, by replacement of one or more carbon-carbon single bonds with a carbon-carbon double bond or a carbon-carbon triple bond.

In an embodiment of the compounds of the invention, R$_{10}$, or at least one of R$_{11}$ and R$_{12}$, is an optionally substituted β-branched C$_4$-C$_{24}$-alkyl, C$_4$-C$_{24}$-alkenyl or C$_4$-C$_{24}$-alkynyl, preferably optionally substituted β-branched C$_7$-C$_{24}$-alkyl, C$_7$-C$_{24}$-alkenyl or C$_7$-C$_{24}$-alkynyl. Suitable examples of β-branched alkyl groups include 2-methyl-C$_3$-C$_{23}$-alkyl and 2,2-dimethyl-C$_3$-C$_{22}$-alkyl, including 2-methylpropyl; 2,2-dimethylpropyl; 2-methylbutyl; 2,2-dimethylbutyl; 2-methylpentyl; 2,2-dimethylpentyl; and 2-ethyl-2-methylbutyl.

In an embodiment of the compounds of the invention, R$_{10}$, or at least one of R$_{11}$ and R$_{12}$, is an optionally substituted aryl-C$_1$-C$_{24}$-alkyl group, such as a phenyl-C$_1$-C$_{24}$-alkyl group. In another embodiment, R$_{10}$ is optionally substituted C$_1$-C$_{24}$-alkylaryl, optionally substituted C$_1$-C$_{24}$-alkenylaryl or optionally substituted C$_1$-C$_{24}$-alkynylaryl.

In an embodiment of the compounds of the invention, R$_5$ is —CH(R$_8$)—OPO$_3$MY or —CH(R$_8$)—OP(O)$_2$(OR$_{11}$)M, where M and Y are each independently a monovalent cation, such as H$^+$, Na$^+$, K$^+$, NH$_4^+$, Cs$^+$, or an organic cation such as an organic ammonium ion or a guanidinium ion, including protonated cations of arginine, lysine, diethylamine, ethylene diamine or piperazine. M and Y can also together represent a divalent cation, such as a Zn$^{2+}$, Fe$^{2+}$, Ca$^{2+}$, or Mg$^{2+}$. Preferably, M and Y together are Ca$^{2+}$.

In certain embodiments, $R_5$ is a group defined by one of the structures set forth below.

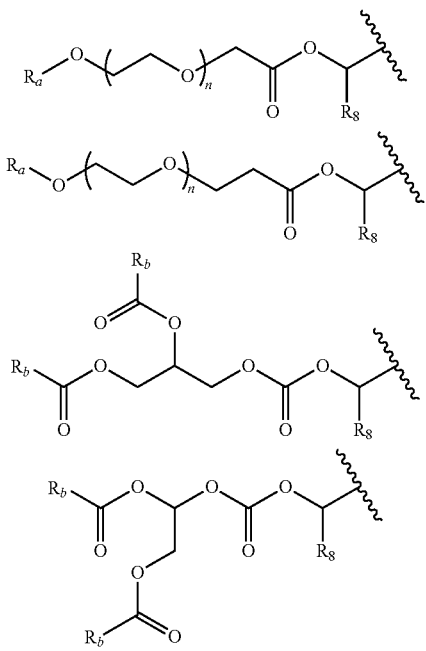

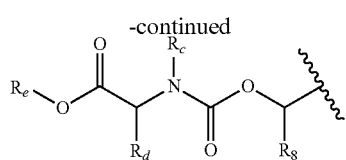

where n is 1 to about 1000, preferably 1 to about 100; $R_a$, $R_b$ and $R_c$ are each independently $C_1$-$C_{24}$-alkyl, substituted $C_1$-$C_{24}$-alkyl, $C_2$-$C_{24}$-alkenyl, substituted $C_2$-$C_{24}$-alkenyl, $C_2$-$C_{24}$-alkynyl, substituted $C_2$-$C_{24}$-alkenyl, $C_3$-$C_{12}$-cycloalkyl, substituted $C_3$-$C_{12}$-cycloalkyl, aryl or substituted aryl; $R_c$ is H or substituted or unsubstituted $C_1$-$C_6$-alkyl; $R_d$ is H, substituted or unsubstituted $C_1$-$C_6$-alkyl, substituted or unsubstituted aryl-$C_1$-$C_6$-alkyl or substituted or unsubstituted heteroaryl-$C_1$-$C_6$-alkyl; and $R_8$ is as defined above and is preferably hydrogen. Preferably $R_a$, $R_b$ and $R_c$ are each $C_1$-$C_{24}$-alkyl. Preferably $R_d$ is the side chain of one of the twenty naturally occurring amino acids, more preferably a neutral or hydrophobic side chain, such as hydrogen, methyl, isopropyl, isobutyl, benzyl, indolylmethyl, and sec-butyl. $R_c$ and $R_d$ can also, together with the carbon and nitrogen atoms to which they are attached, form a heterocycloalkyl group, preferably a pyrrolidine group.

In preferred embodiments, variable $R_5$ in any of Formulas I, X, XI, XII, XIII, XIV, XV and XVI is selected from the groups set forth in the Table 1 below.

TABLE 1

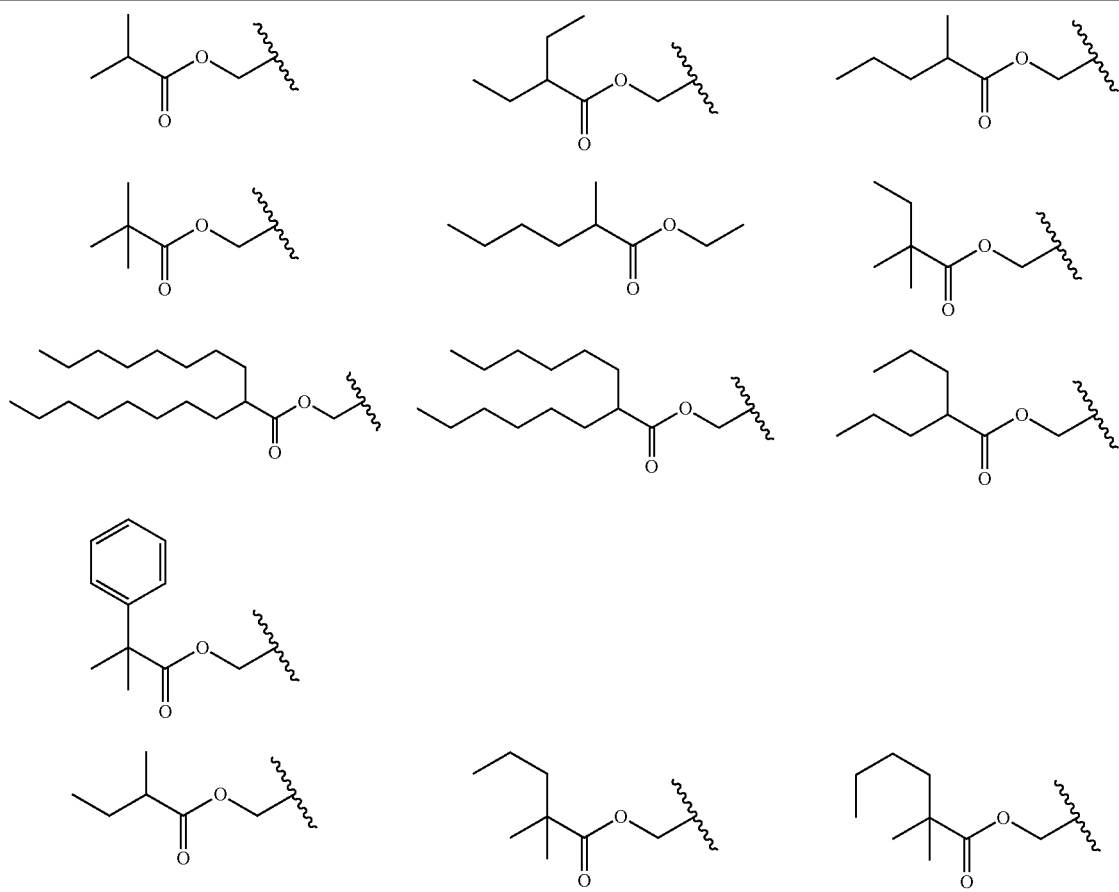

TABLE 1-continued
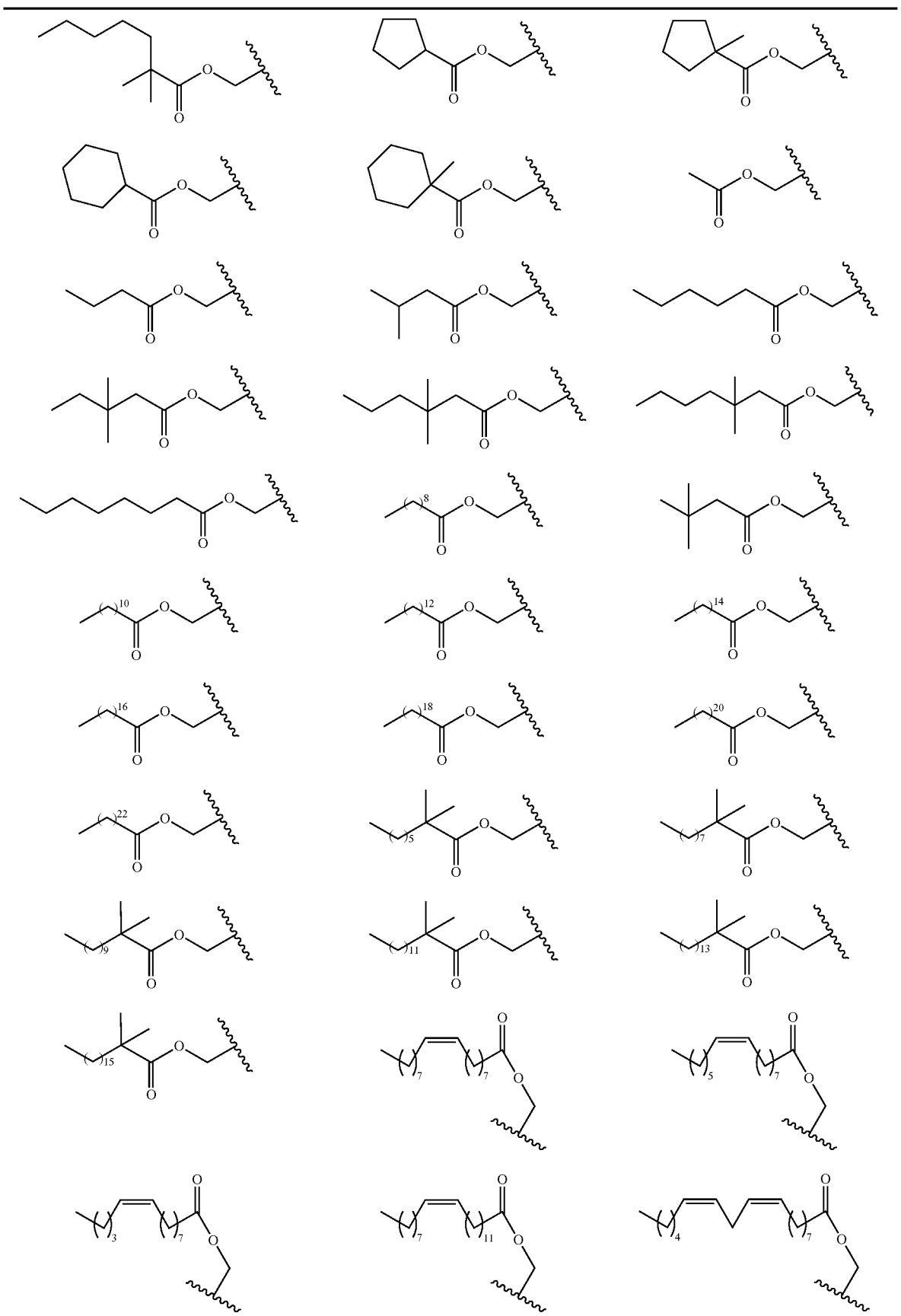

TABLE 1-continued
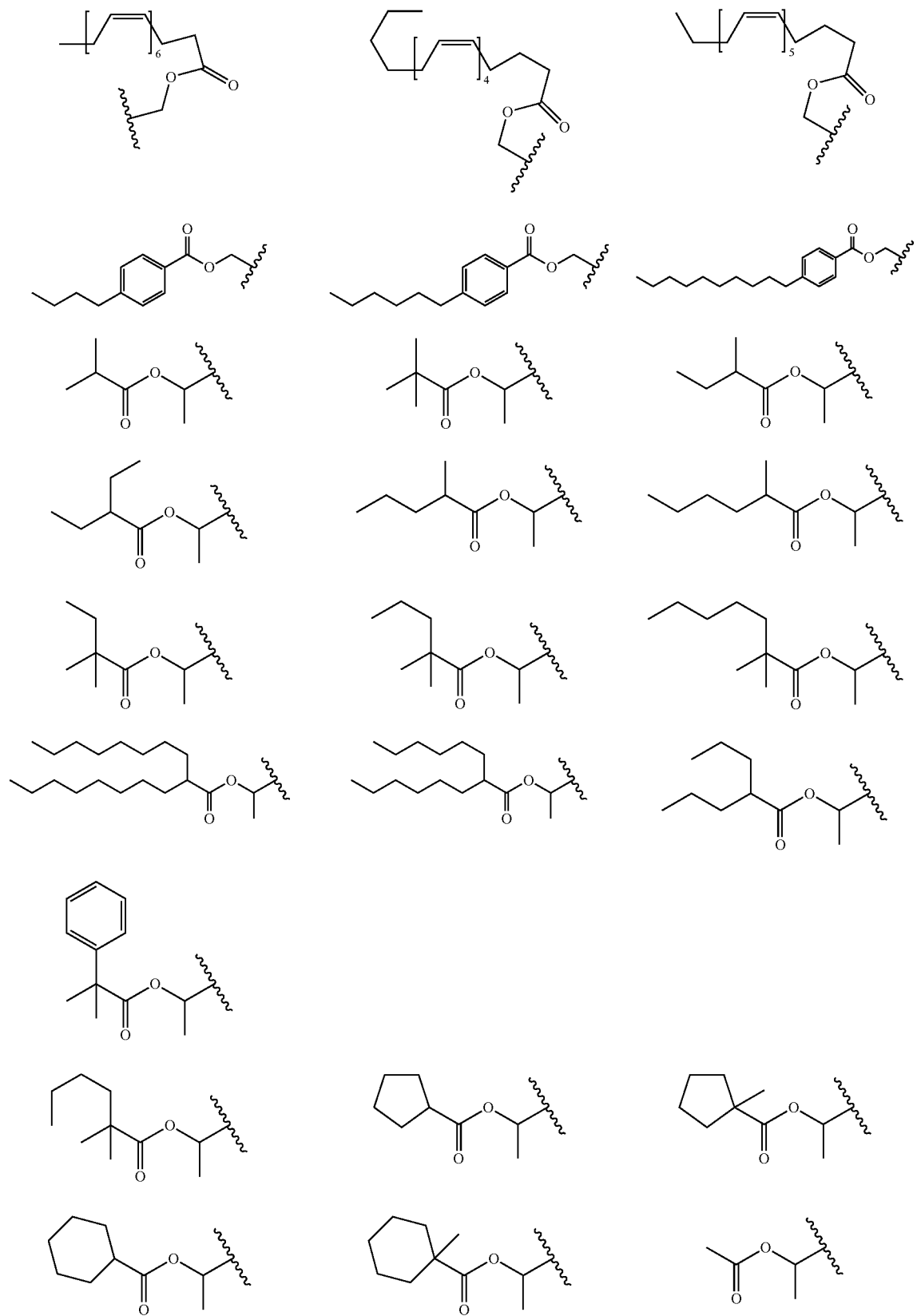

TABLE 1-continued
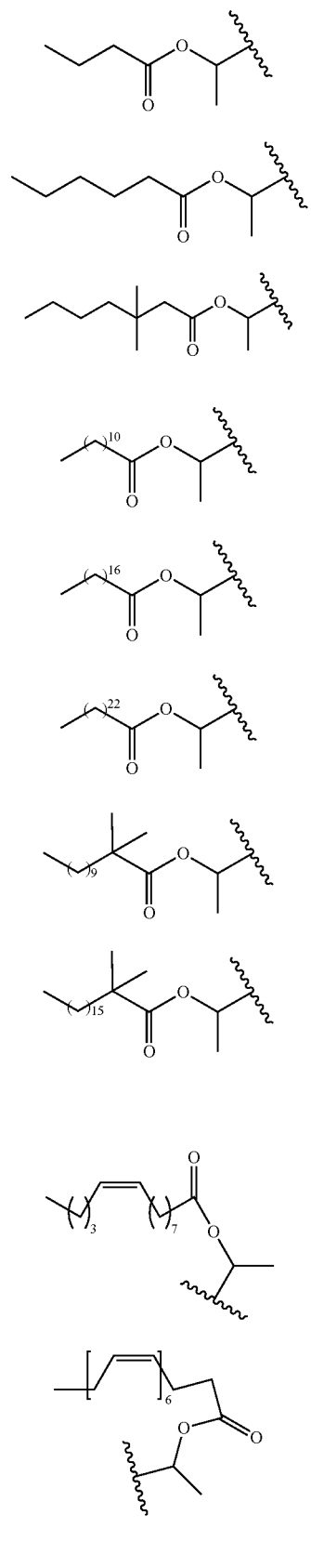
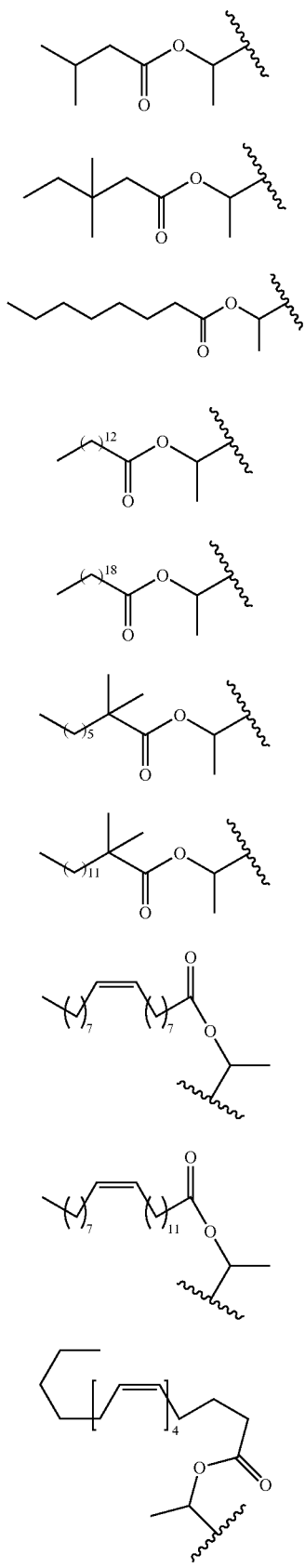
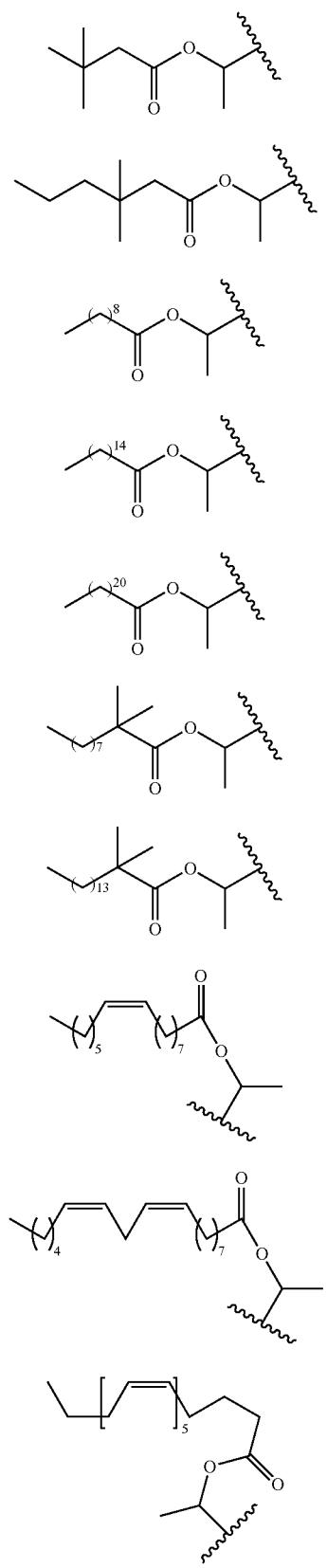

TABLE 1-continued
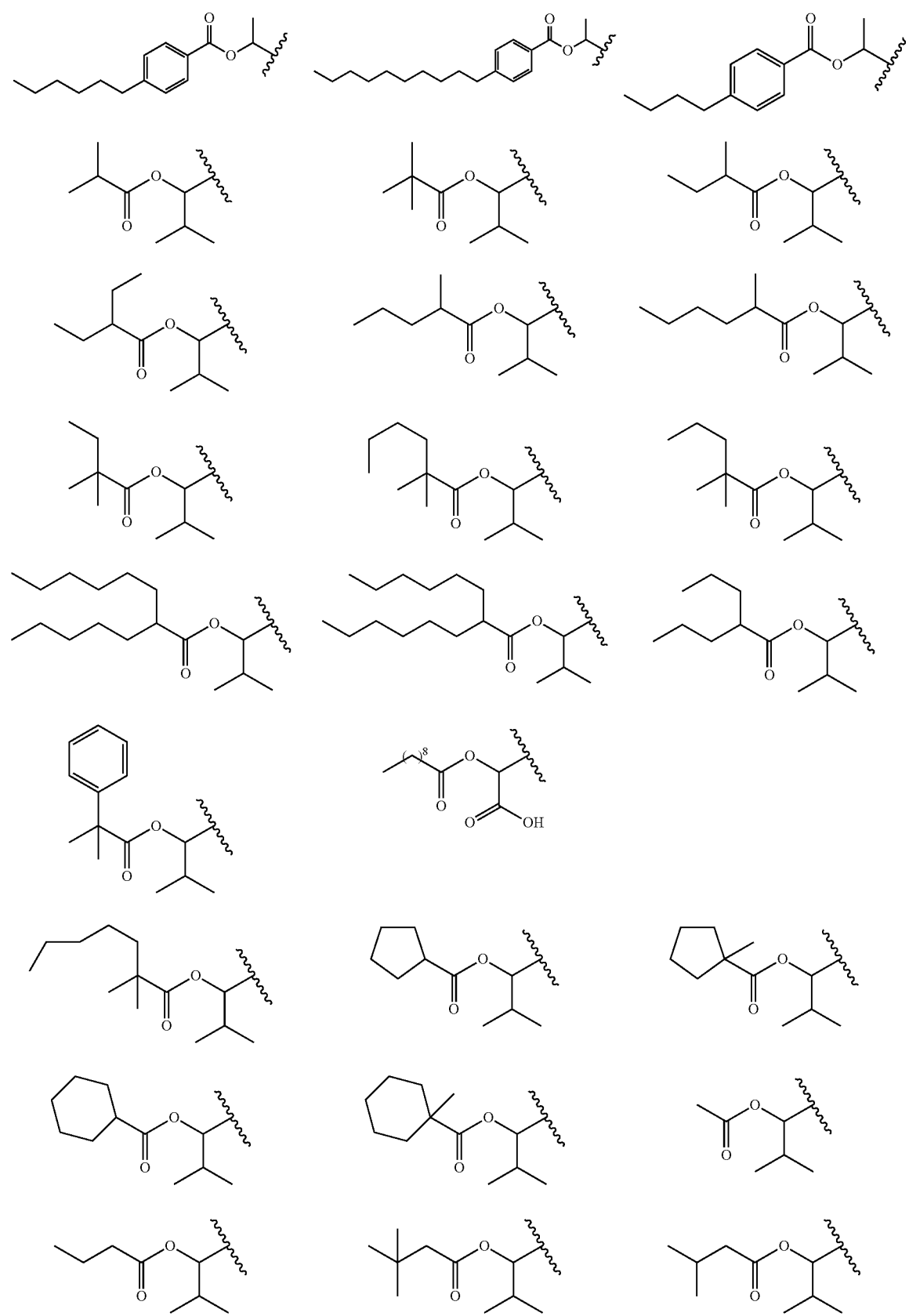

TABLE 1-continued
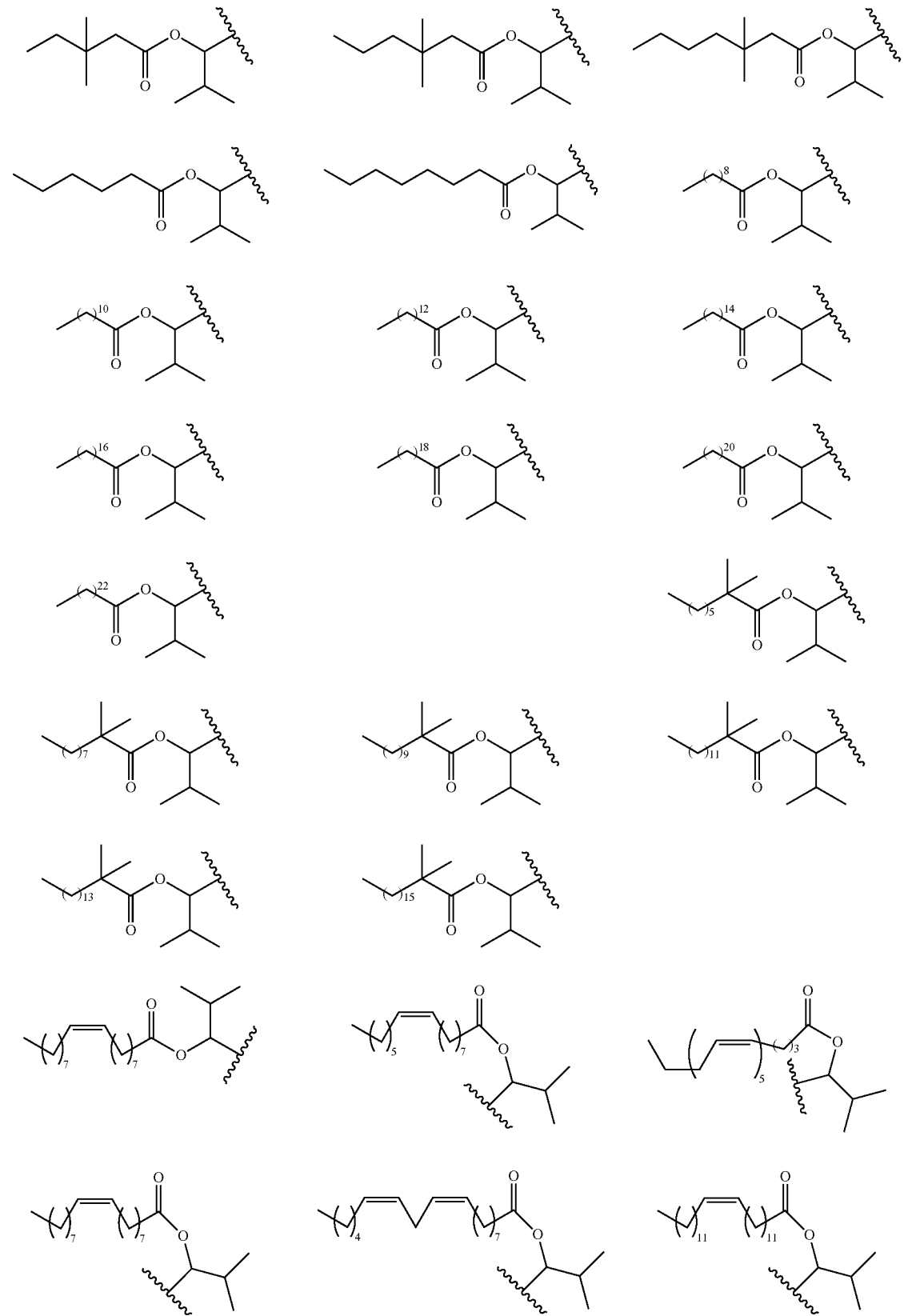

TABLE 1-continued
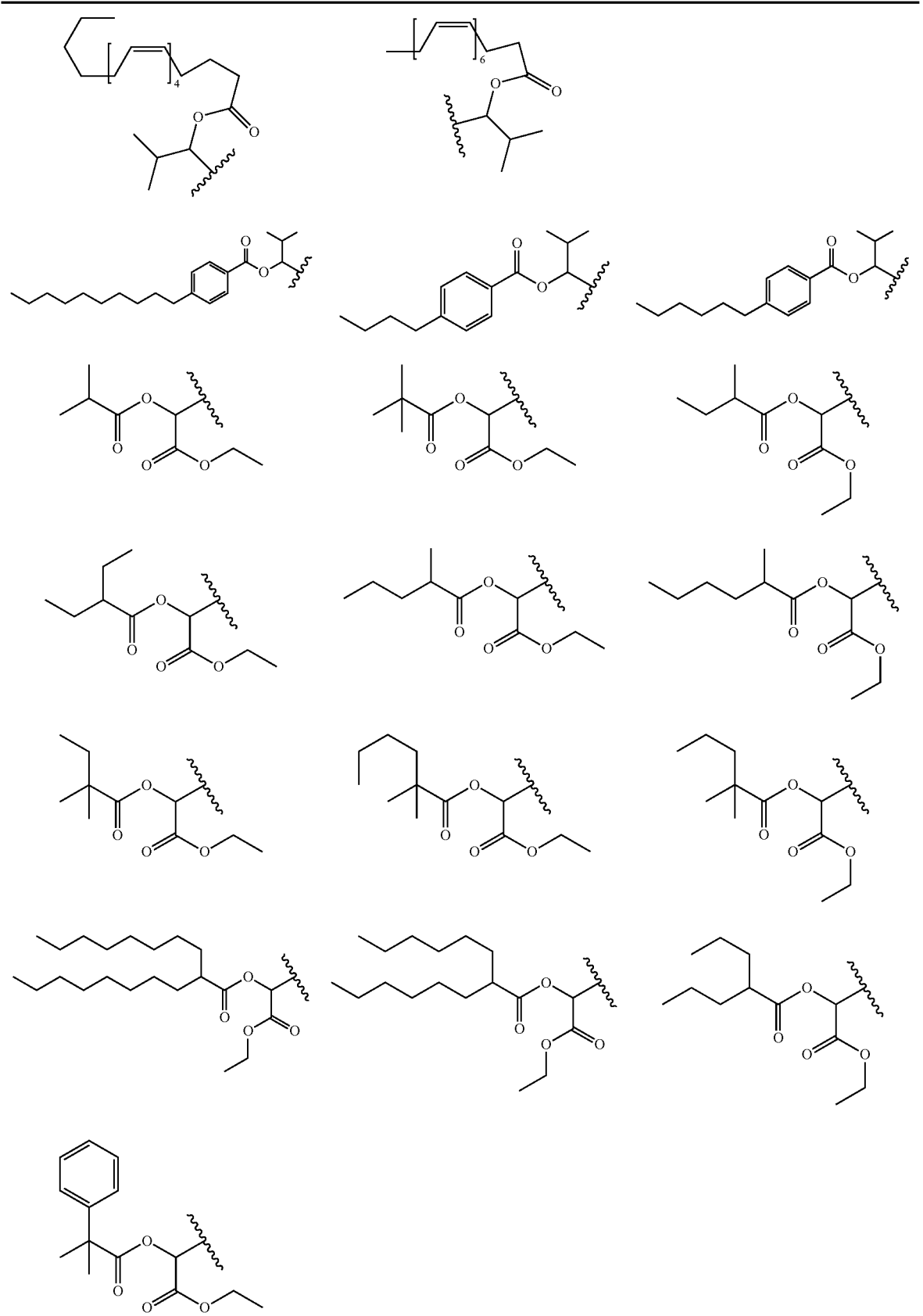

TABLE 1-continued
| | | |
|---|---|---|
| 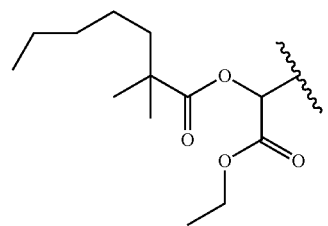 [SMILES: *C(OC(=O)C(C)(C)CCCCC)C(=O)OCC] | 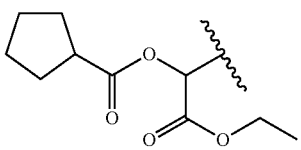 [SMILES: *C(OC(=O)C1CCCC1)C(=O)OCC] | 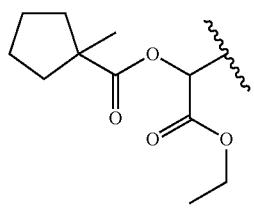 [SMILES: *C(OC(=O)C1(C)CCCC1)C(=O)OCC] |
| 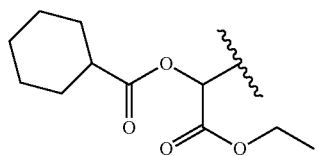 [SMILES: *C(OC(=O)C1CCCCC1)C(=O)OCC] | 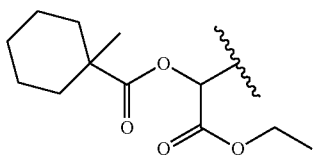 [SMILES: *C(OC(=O)C1(C)CCCCC1)C(=O)OCC] | 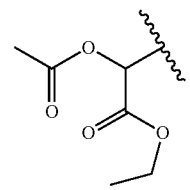 [SMILES: *C(OC(C)=O)C(=O)OCC] |
| 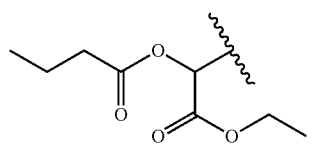 [SMILES: *C(OC(=O)CCC)C(=O)OCC] | 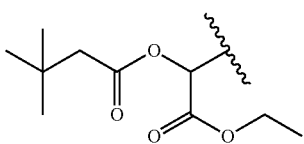 [SMILES: *C(OC(=O)CC(C)(C)C)C(=O)OCC] | 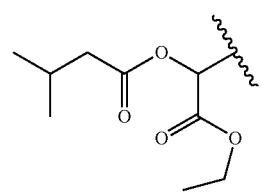 [SMILES: *C(OC(=O)CC(C)C)C(=O)OCC] |
| 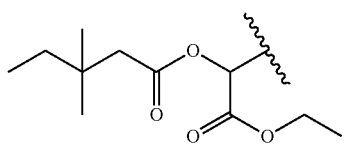 [SMILES: *C(OC(=O)CC(C)(C)CC)C(=O)OCC] | 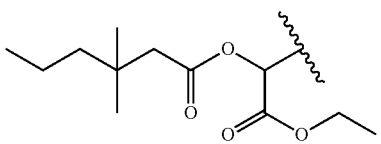 [SMILES: *C(OC(=O)CC(C)(C)CCC)C(=O)OCC] | 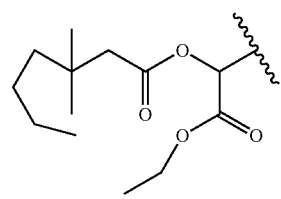 [SMILES: *C(OC(=O)CC(C)(C)CCCC)C(=O)OCC] |
| 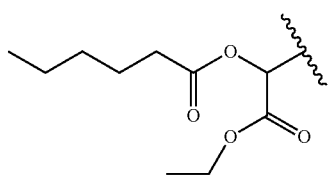 [SMILES: *C(OC(=O)CCCCC)C(=O)OCC] | 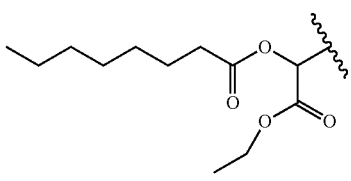 [SMILES: *C(OC(=O)CCCCCCC)C(=O)OCC] | 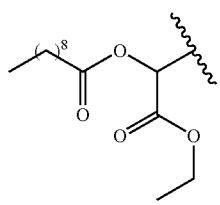 |
| 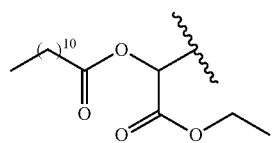 | 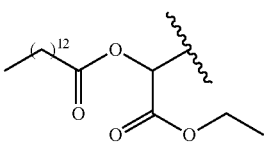 | 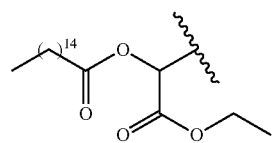 |
| 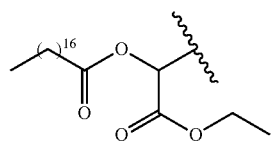 | 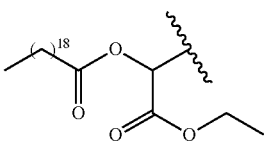 | 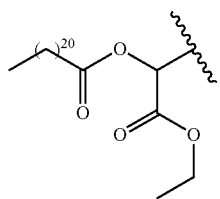 |
| 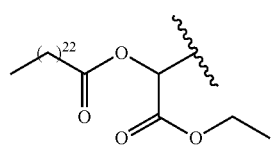 | | 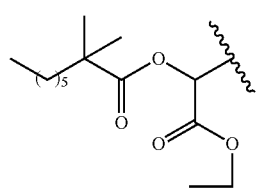 |

TABLE 1-continued
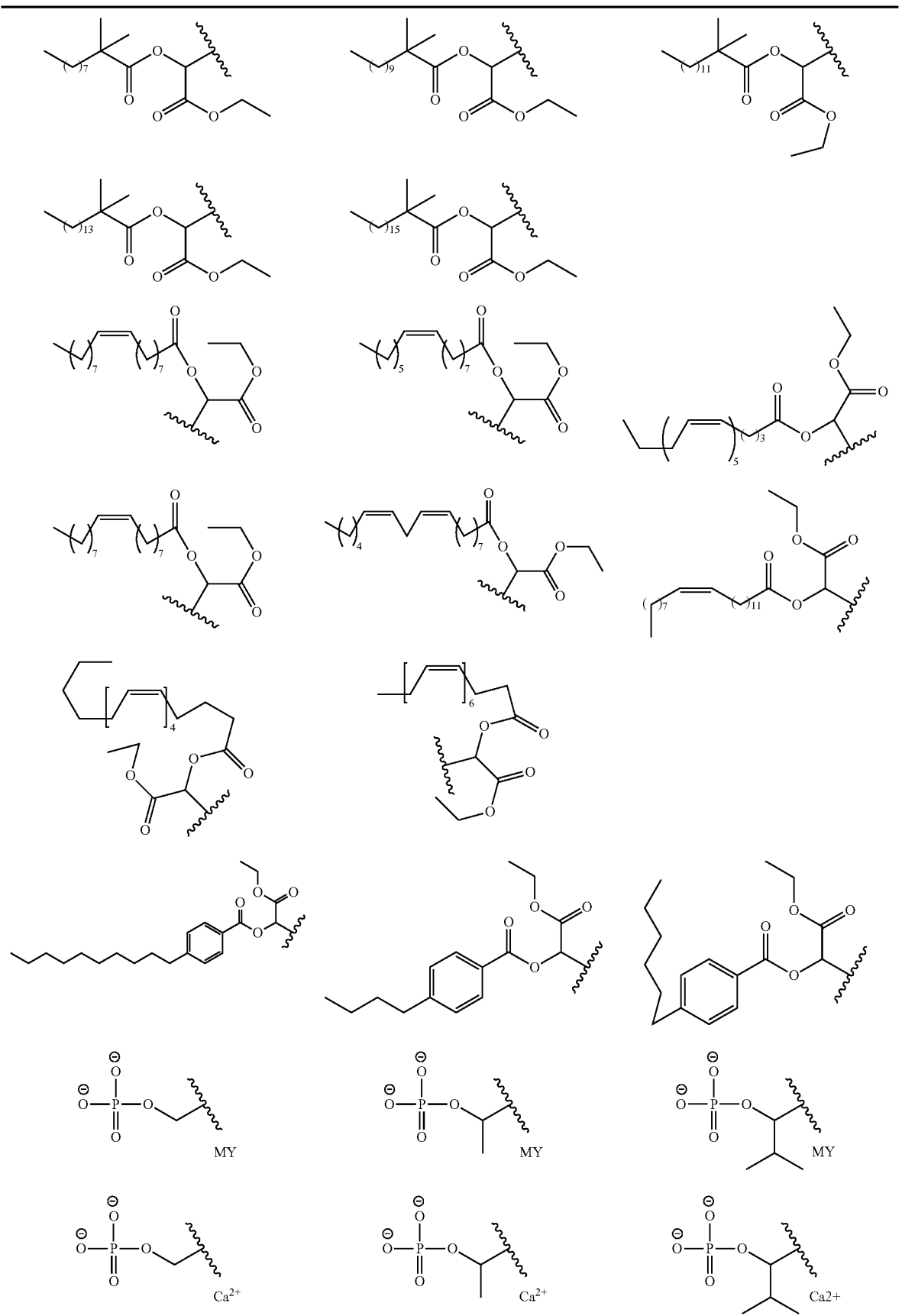

TABLE 1-continued
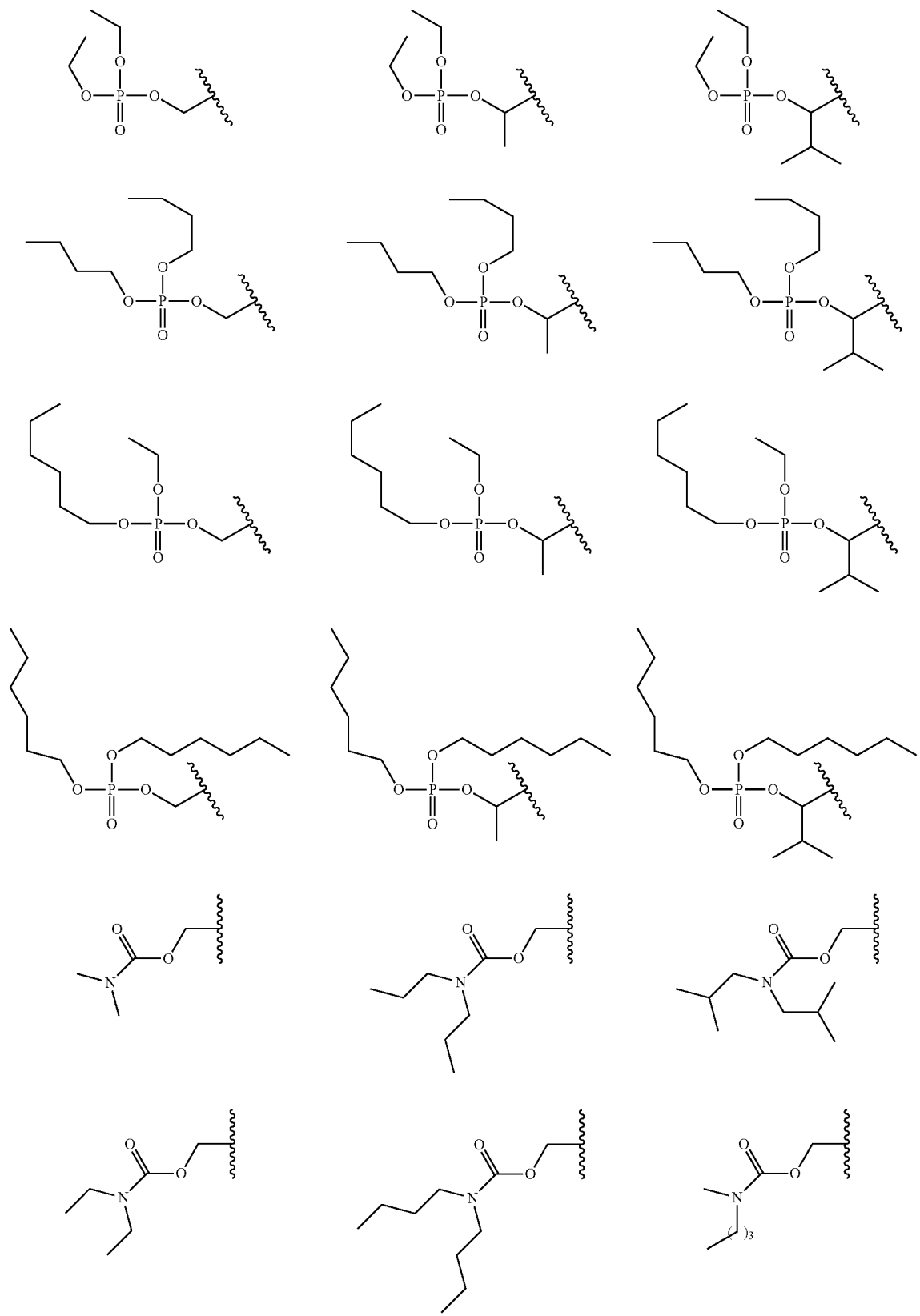

TABLE 1-continued
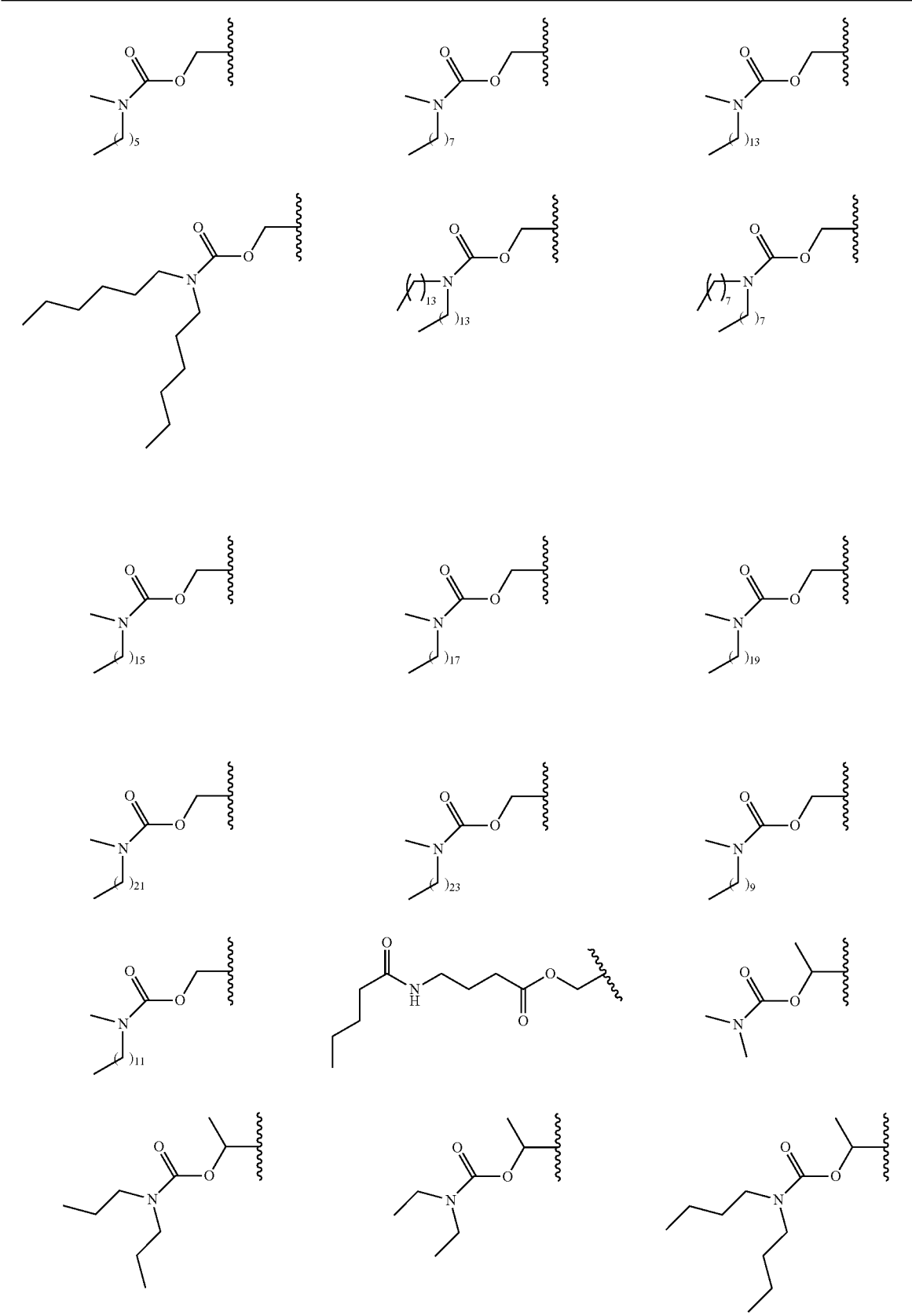

TABLE 1-continued
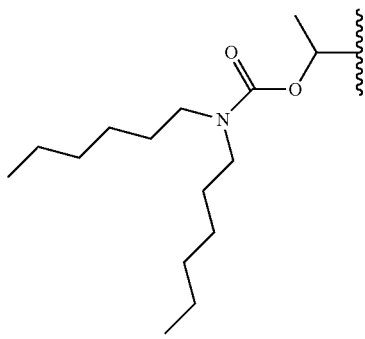 [SMILES: *C(C)OC(=O)N(CCCCCC)CCCCCC] 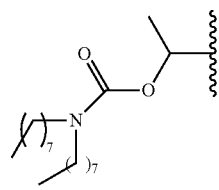 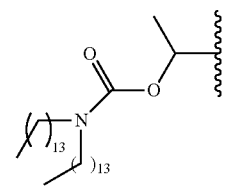
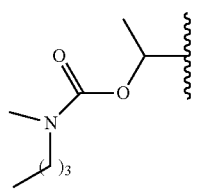 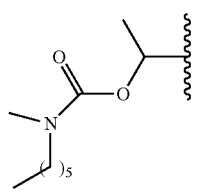 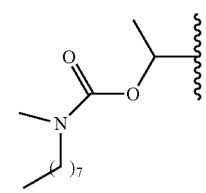
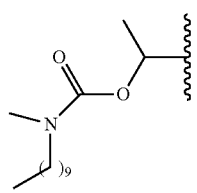 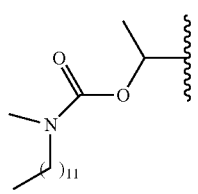 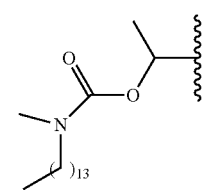
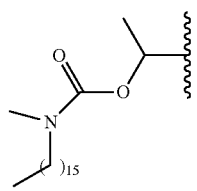 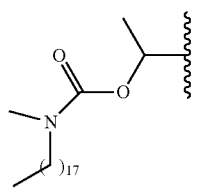 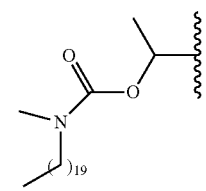
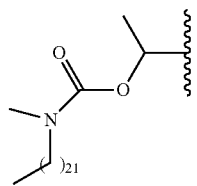 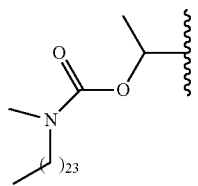 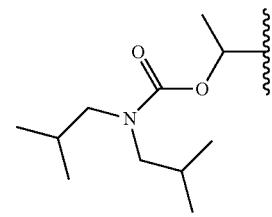 [SMILES: *C(C)OC(=O)N(CC(C)C)CC(C)C]
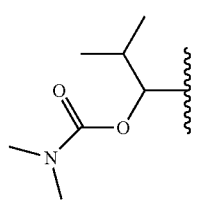 [SMILES: *C(OC(=O)N(C)C)C(C)C] 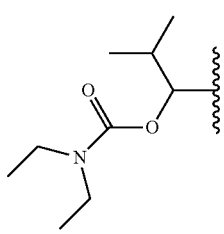 [SMILES: *C(OC(=O)N(CC)CC)C(C)C] 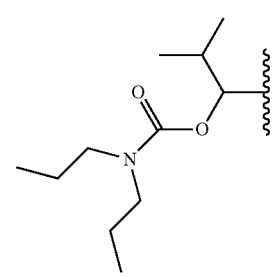 [SMILES: *C(OC(=O)N(CCC)CCC)C(C)C]

TABLE 1-continued
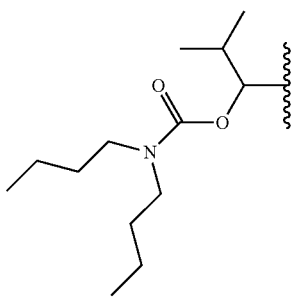 [SMILES: *C(OC(=O)N(CCCC)CCCC)C(C)C] 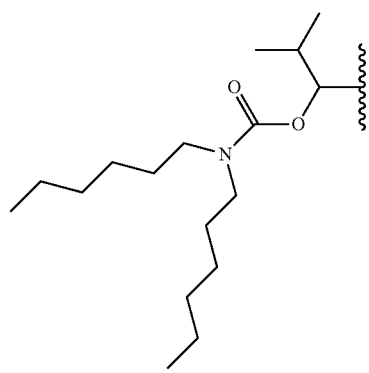 [SMILES: *C(OC(=O)N(CCCCCC)CCCCCC)C(C)C] 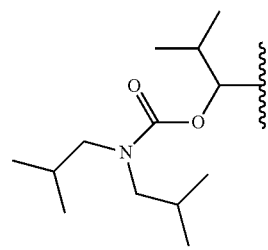 [SMILES: *C(OC(=O)N(CC(C)C)CC(C)C)C(C)C]
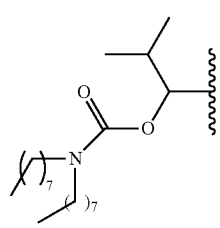 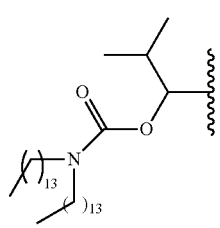 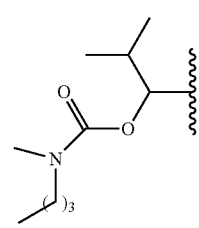
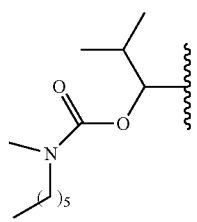 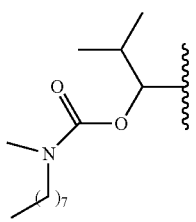 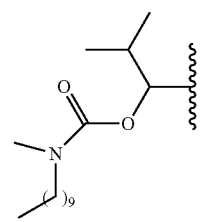
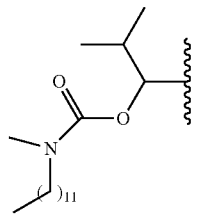 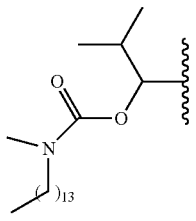 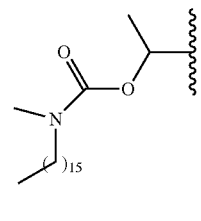
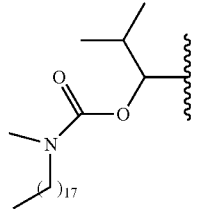 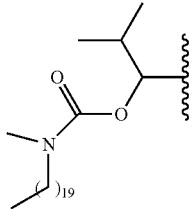 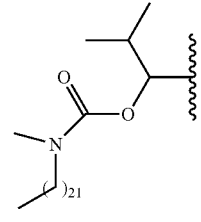
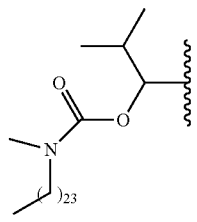

TABLE 1-continued
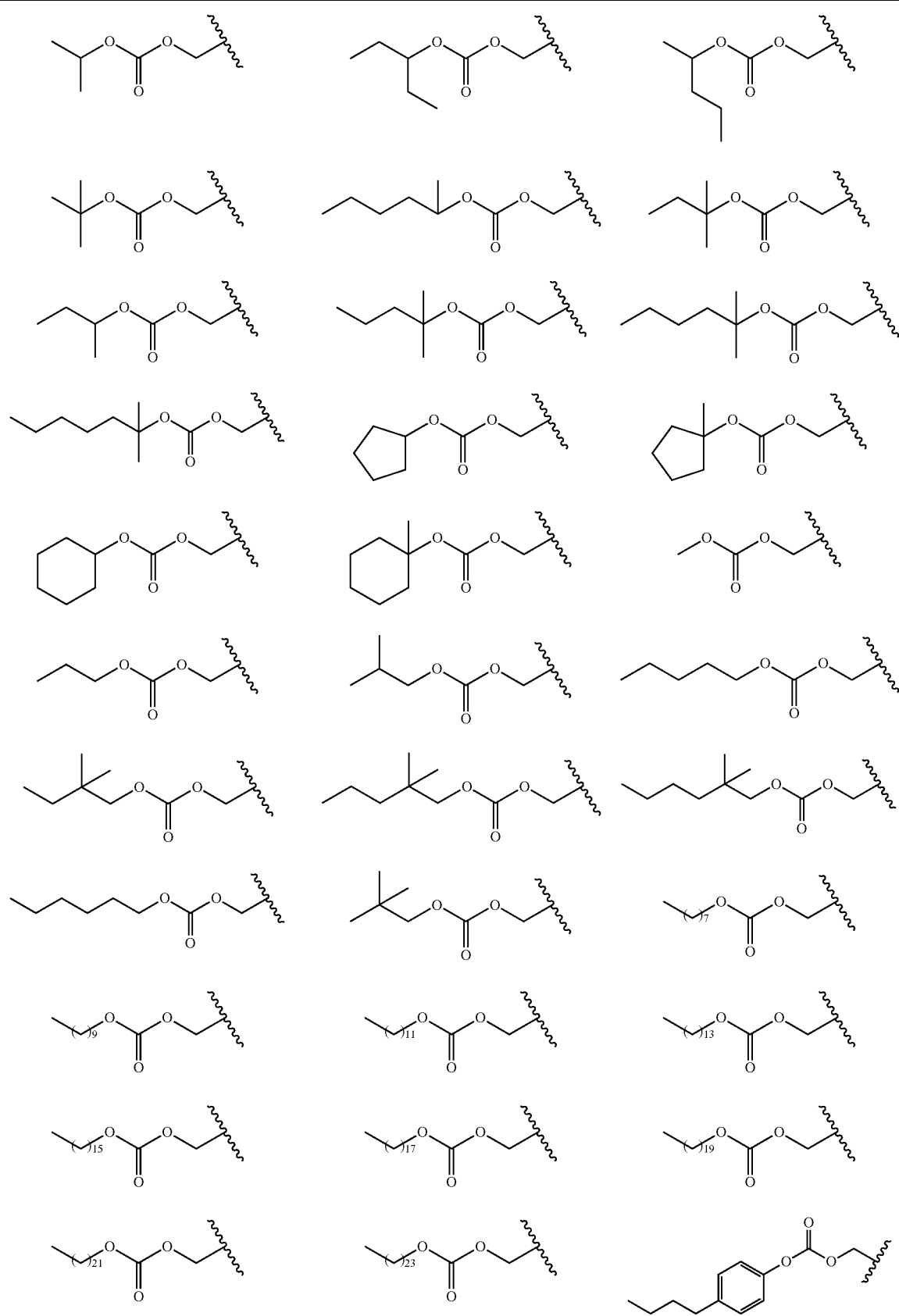

TABLE 1-continued
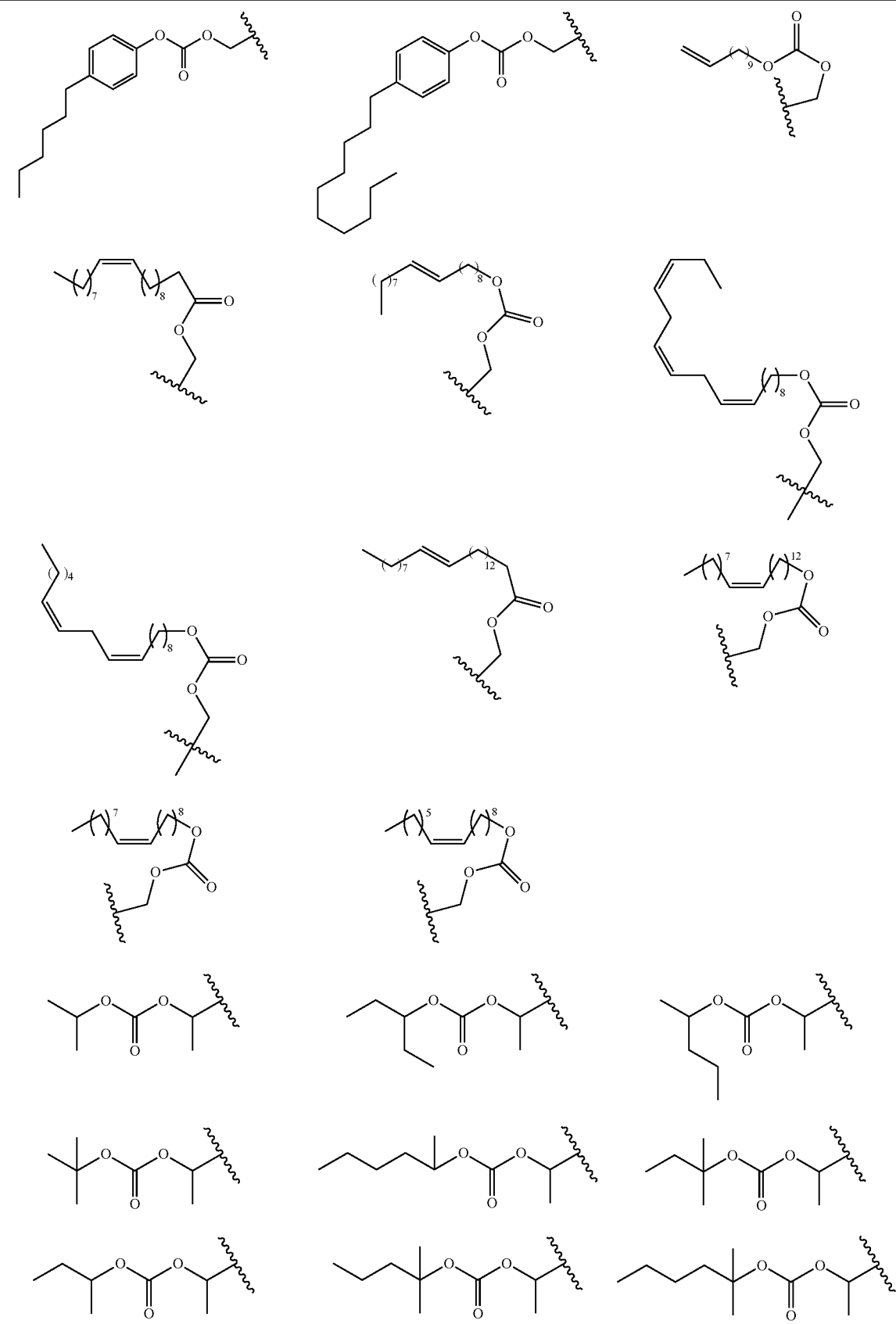

TABLE 1-continued
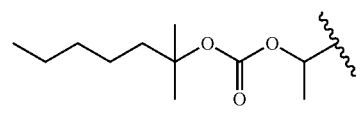 [SMILES: *C(C)OC(=O)OC(C)(C)CCCCC] 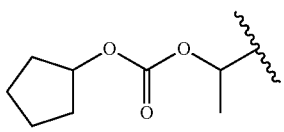 [SMILES: *C(C)OC(=O)OC1CCCC1] 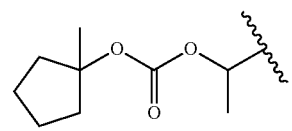 [SMILES: *C(C)OC(=O)OC1(C)CCCC1]
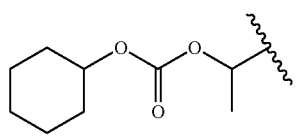 [SMILES: *C(C)OC(=O)OC1CCCCC1] 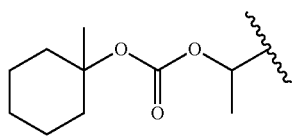 [SMILES: *C(C)OC(=O)OC1(C)CCCCC1] 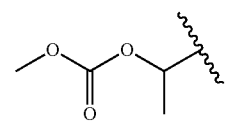 [SMILES: *C(C)OC(=O)OC]
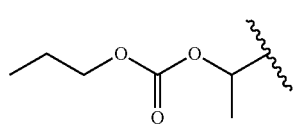 [SMILES: *C(C)OC(=O)OCCC] 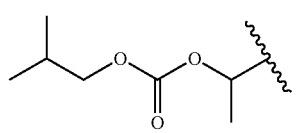 [SMILES: *C(C)OC(=O)OCC(C)C] 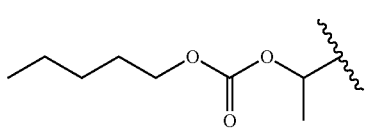 [SMILES: *C(C)OC(=O)OCCCCC]
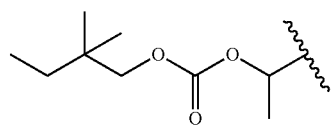 [SMILES: *C(C)OC(=O)OCC(C)(C)CC] 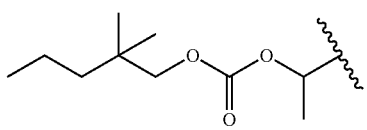 [SMILES: *C(C)OC(=O)OCC(C)(C)CCC] 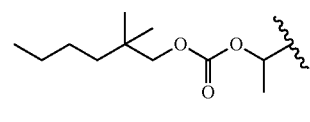 [SMILES: *C(C)OC(=O)OCC(C)(C)CCCC]
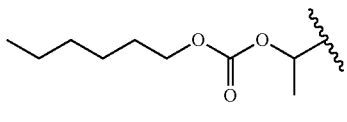 [SMILES: *C(C)OC(=O)OCCCCCC] 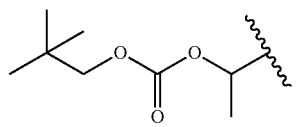 [SMILES: *C(C)OC(=O)OCC(C)(C)C] 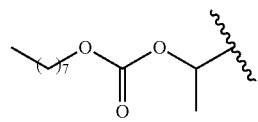
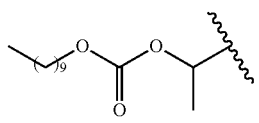 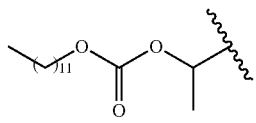 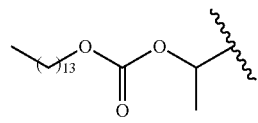
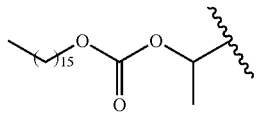 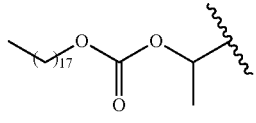 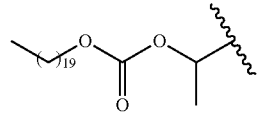
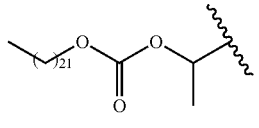 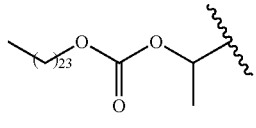 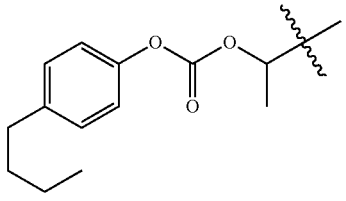 [SMILES: *C(C)OC(=O)Oc1ccc(CCCC)cc1]
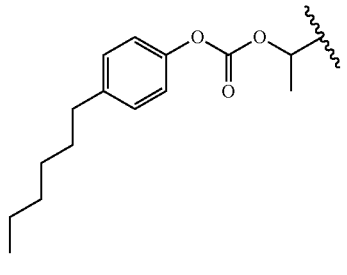 [SMILES: *C(C)OC(=O)Oc1ccc(CCCCCC)cc1] 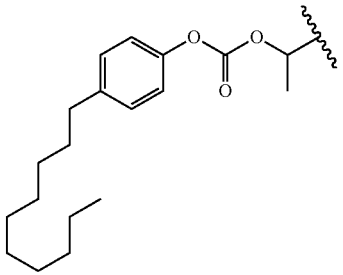 [SMILES: *C(C)OC(=O)Oc1ccc(CCCCCCCCCC)cc1] 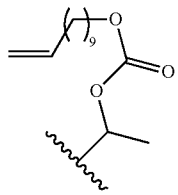

TABLE 1-continued
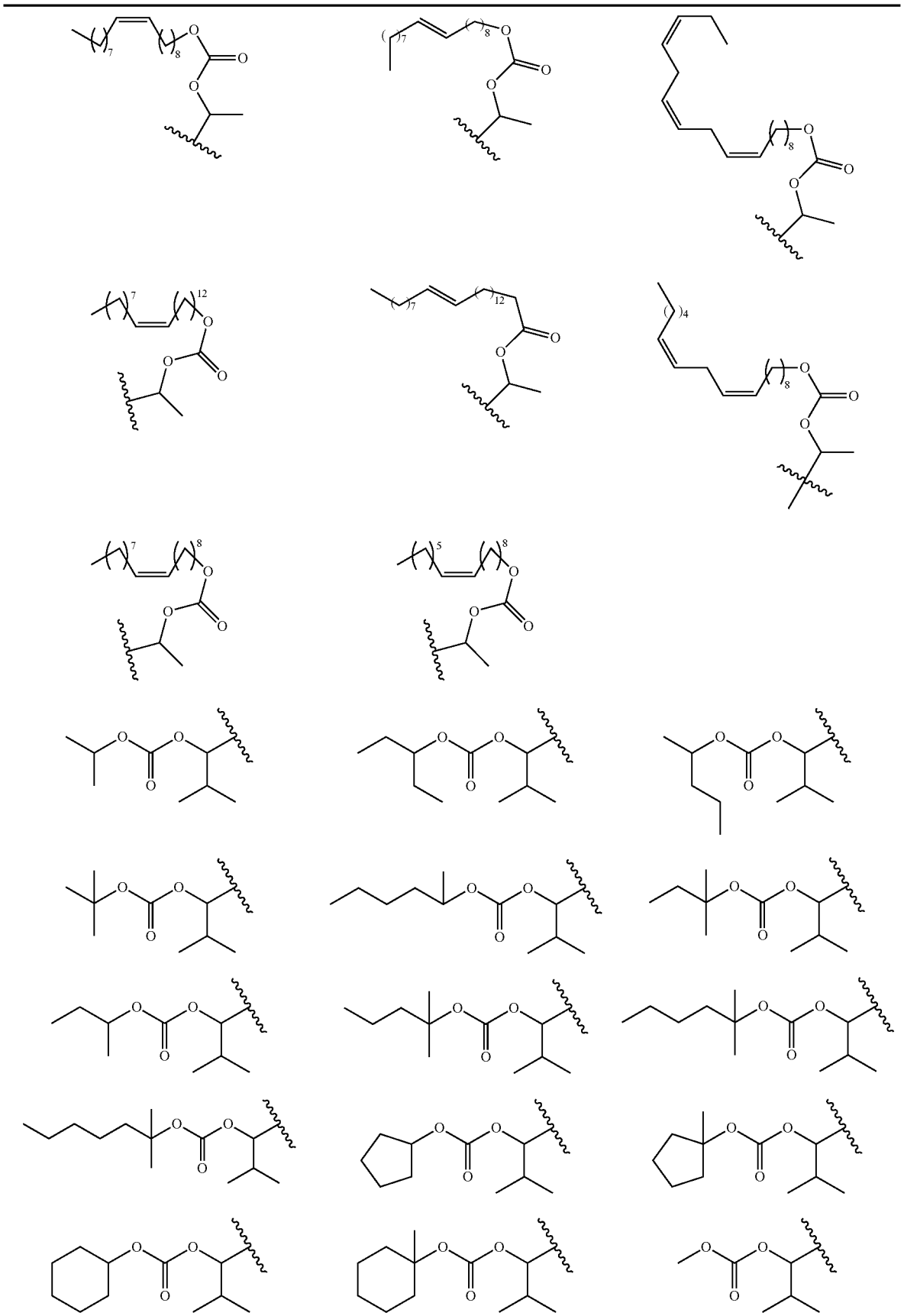

TABLE 1-continued
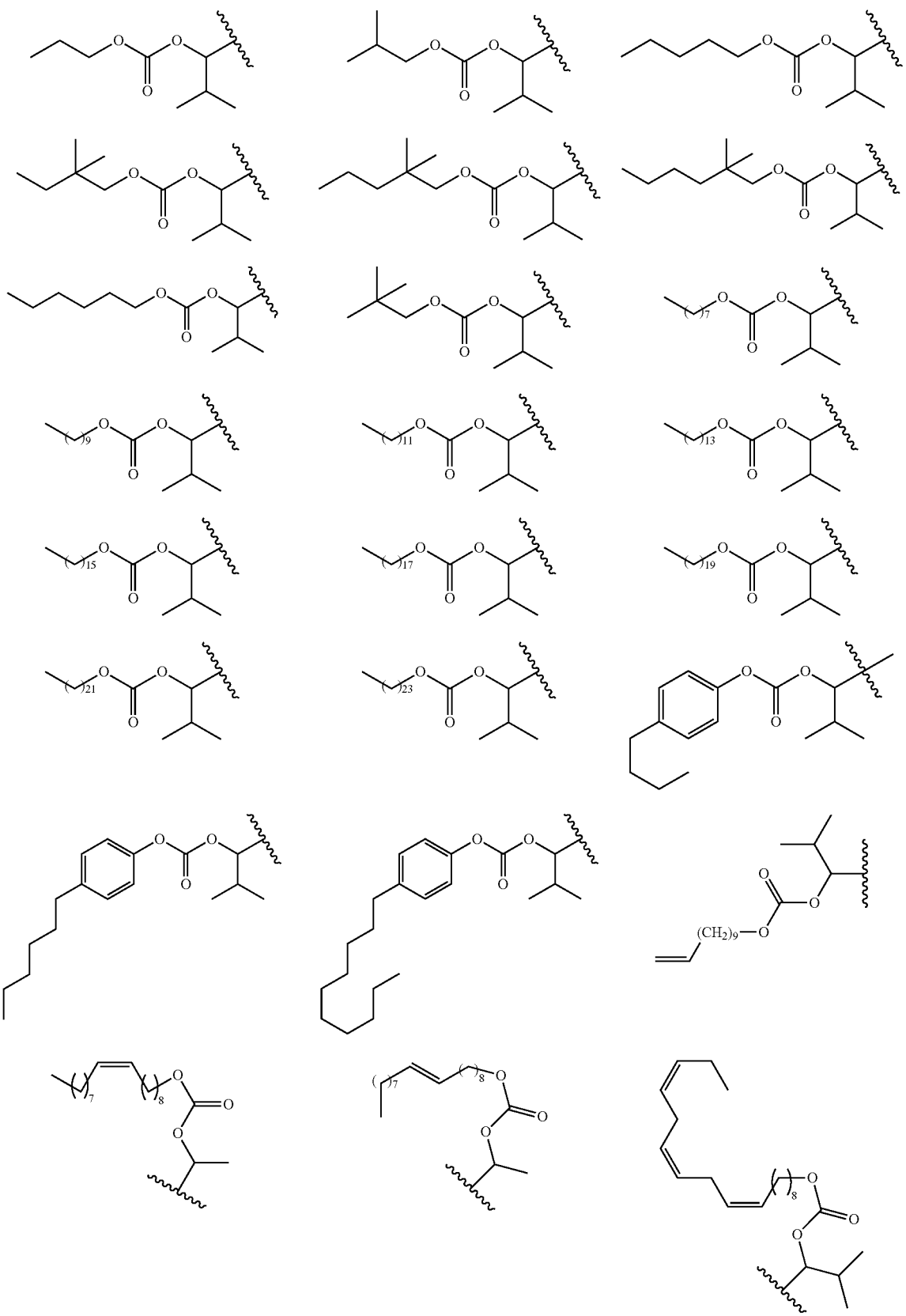

TABLE 1-continued
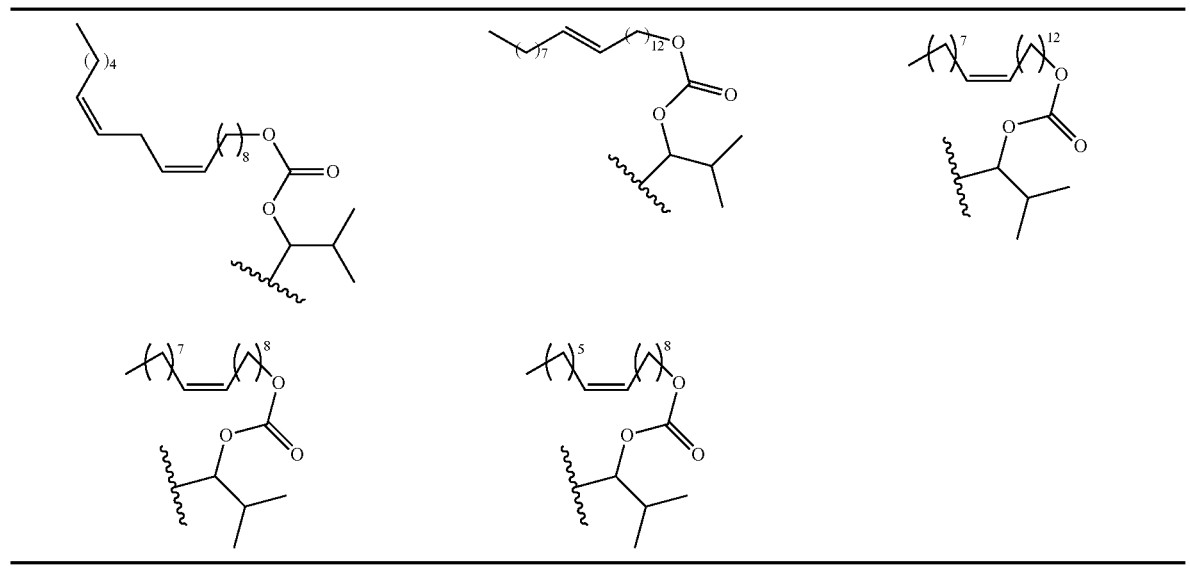
In preferred embodiments, variable $R_5$ in any of Formulas I, X, XI, XII, XIII, XIV, XV and XVI is selected from the group set forth in Tables 2, 3 and 4 below.
TABLE 2
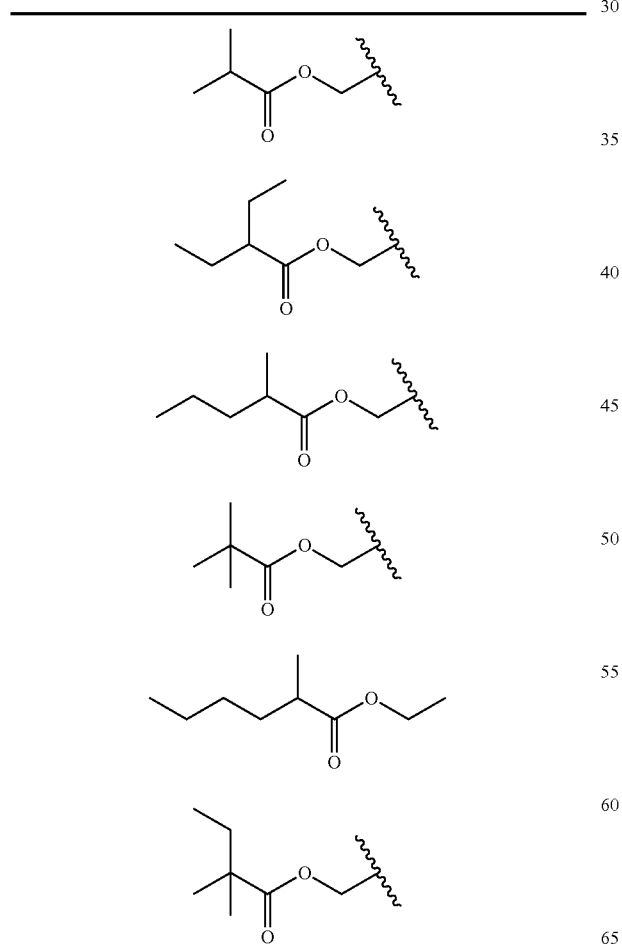
TABLE 2-continued
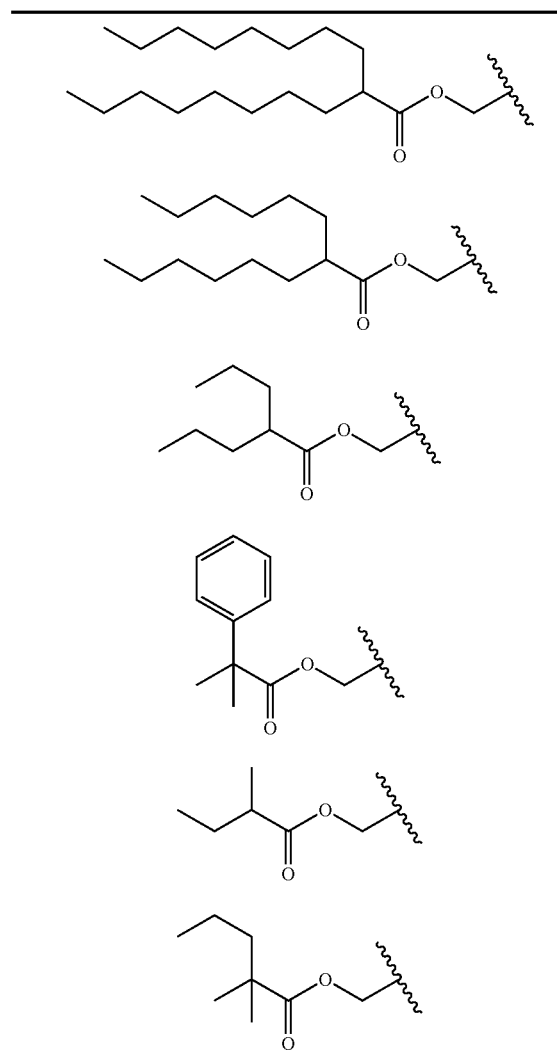

TABLE 2-continued
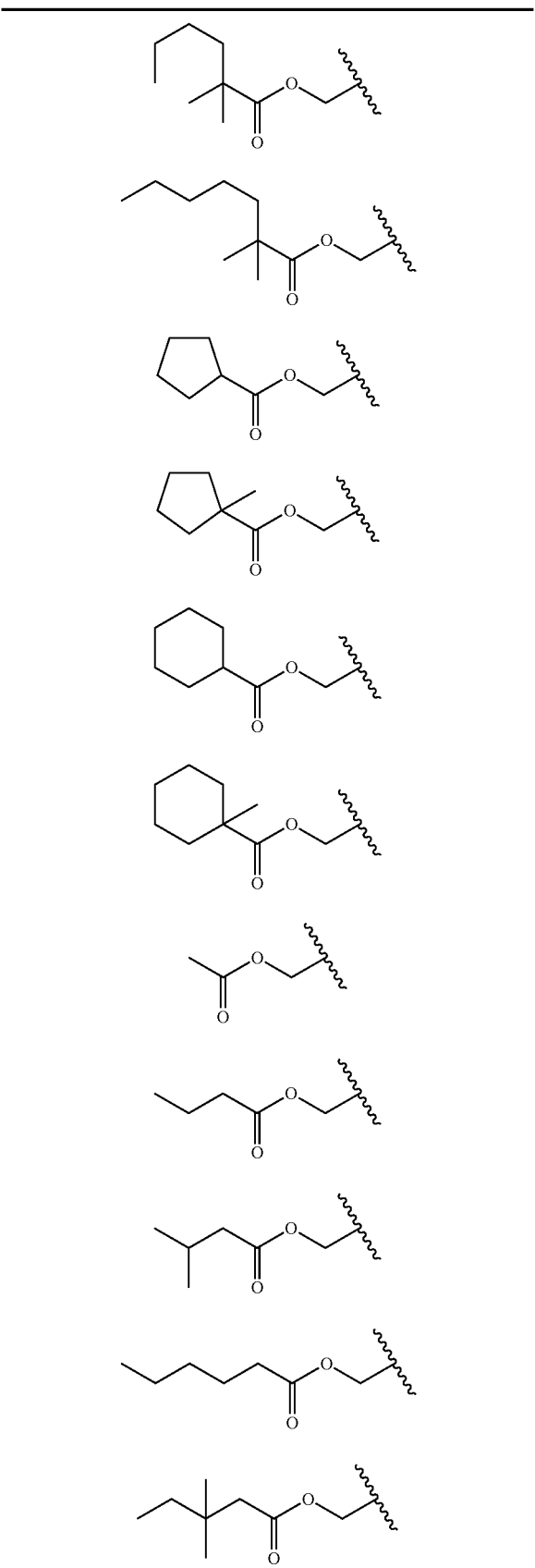
TABLE 2-continued
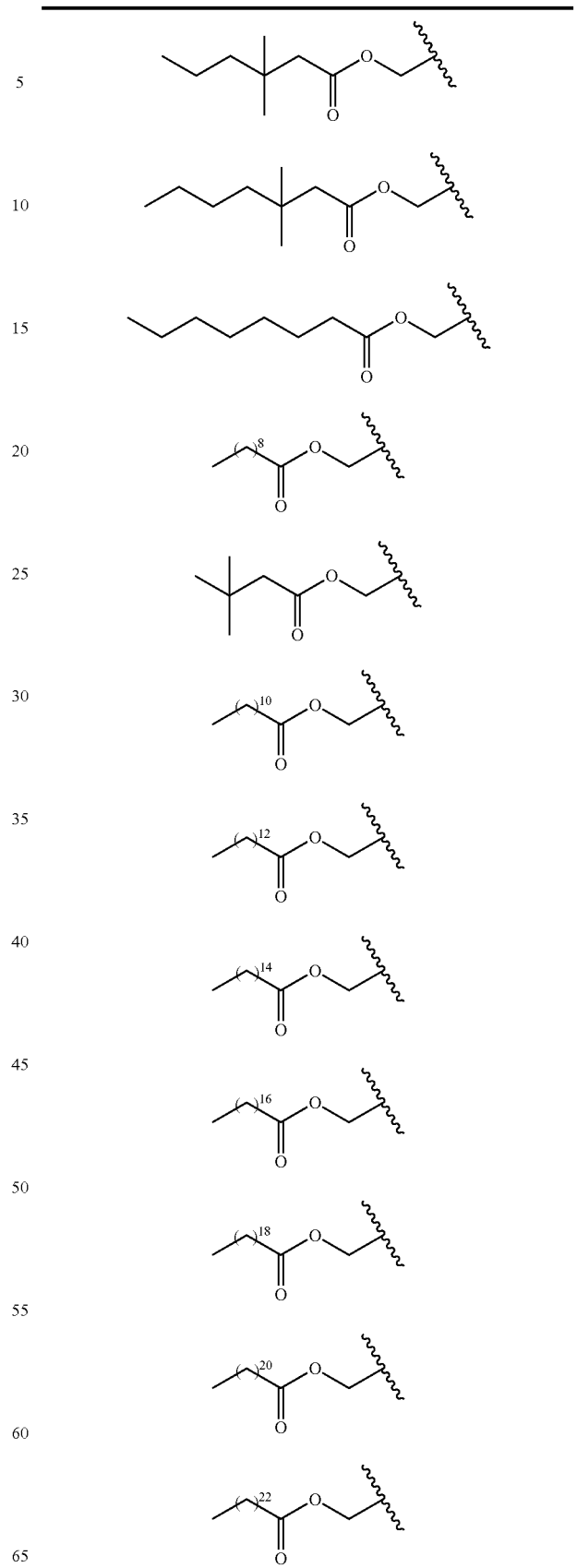

TABLE 2-continued
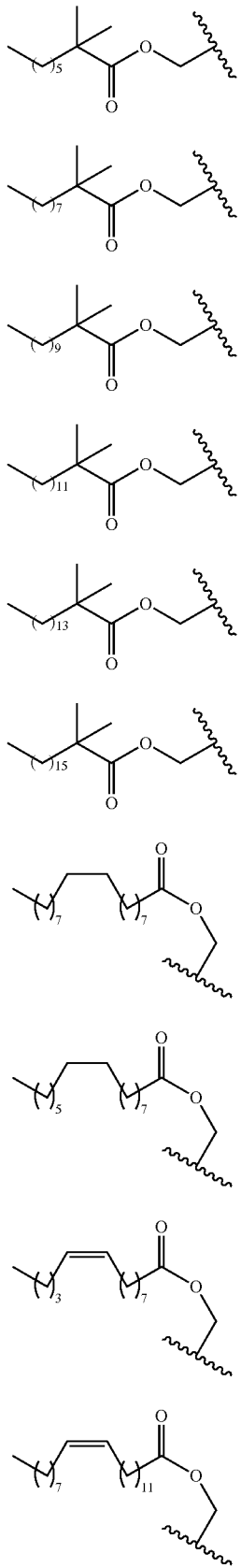
TABLE 2-continued
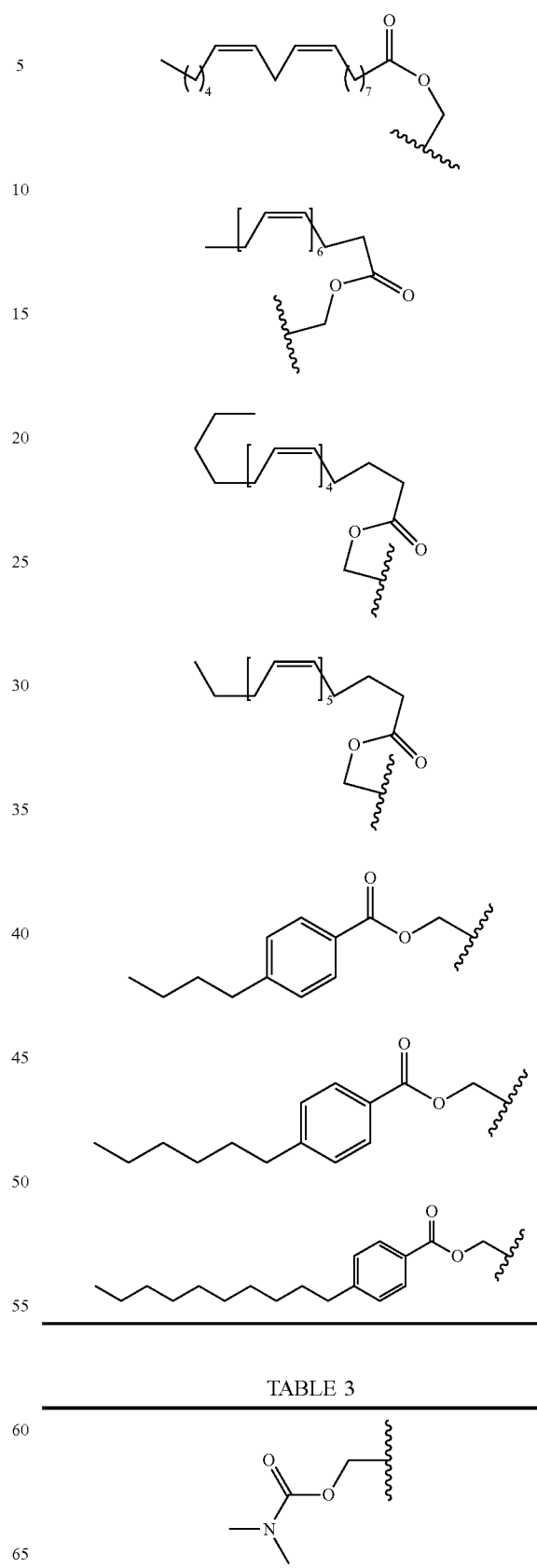
TABLE 3
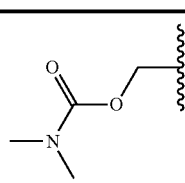

TABLE 3-continued
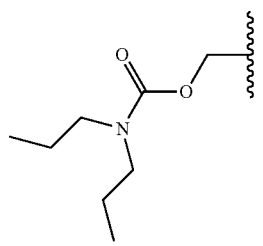 [SMILES: *COC(=O)N(CCC)CCC]
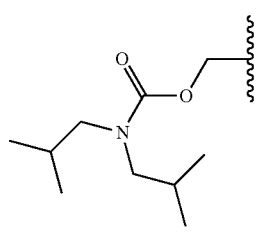 [SMILES: *COC(=O)N(CC(C)C)CC(C)C]
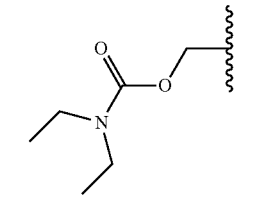 [SMILES: *COC(=O)N(CC)CC]
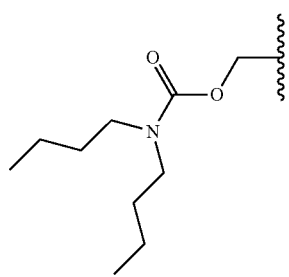 [SMILES: *COC(=O)N(CCCC)CCCC]
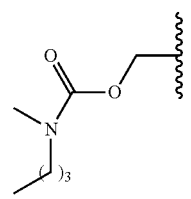
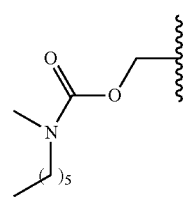
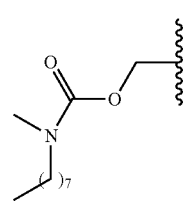
TABLE 3-continued
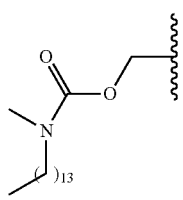
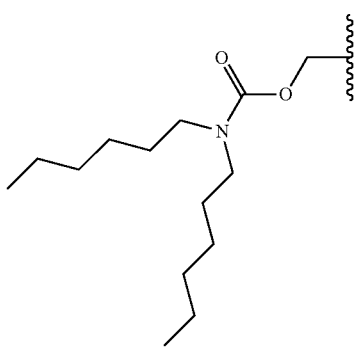 [SMILES: *COC(=O)N(CCCCCC)CCCCCC]
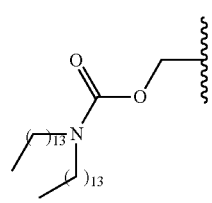
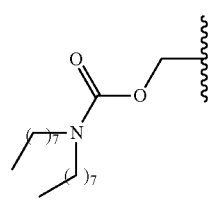
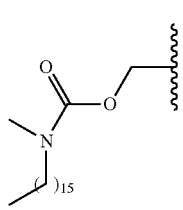
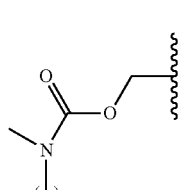
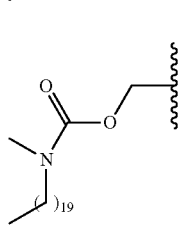

TABLE 3-continued
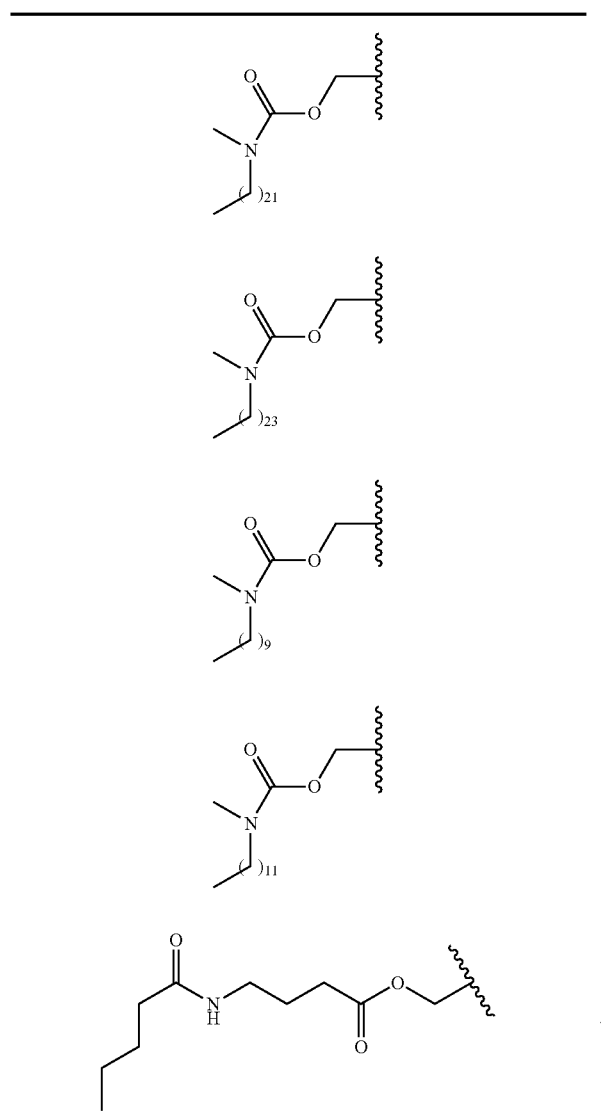
TABLE 4
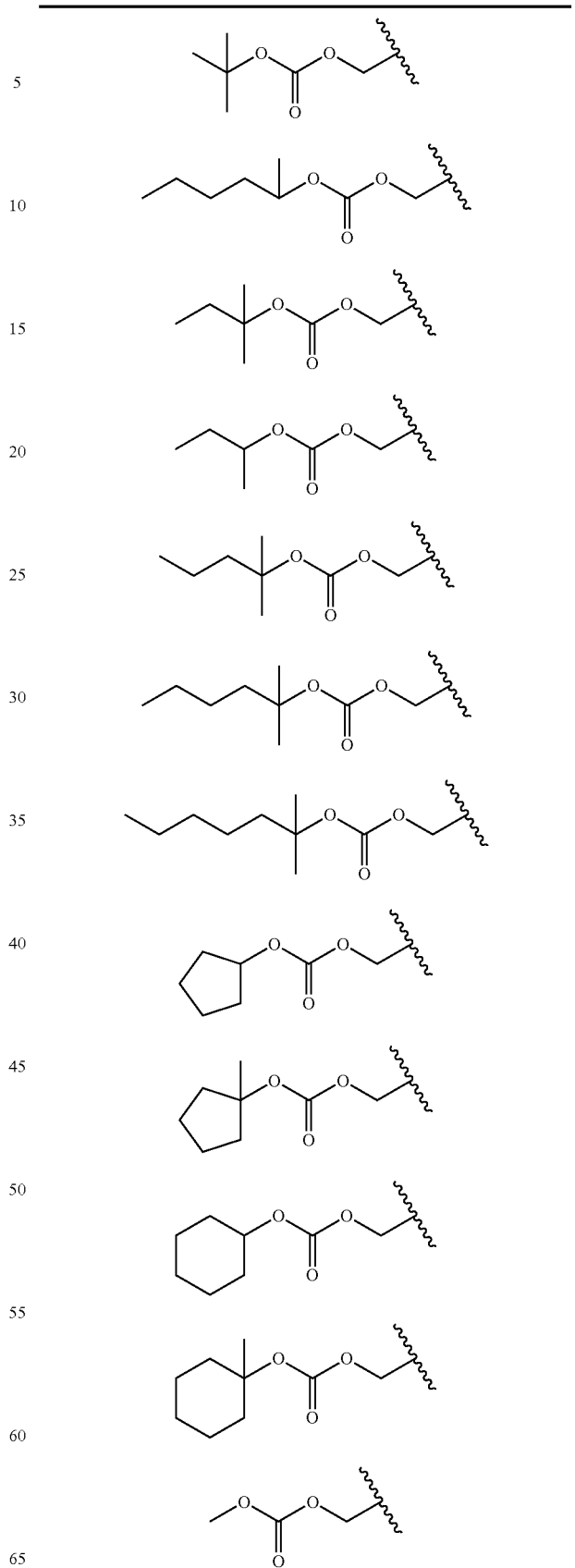

TABLE 4-continued
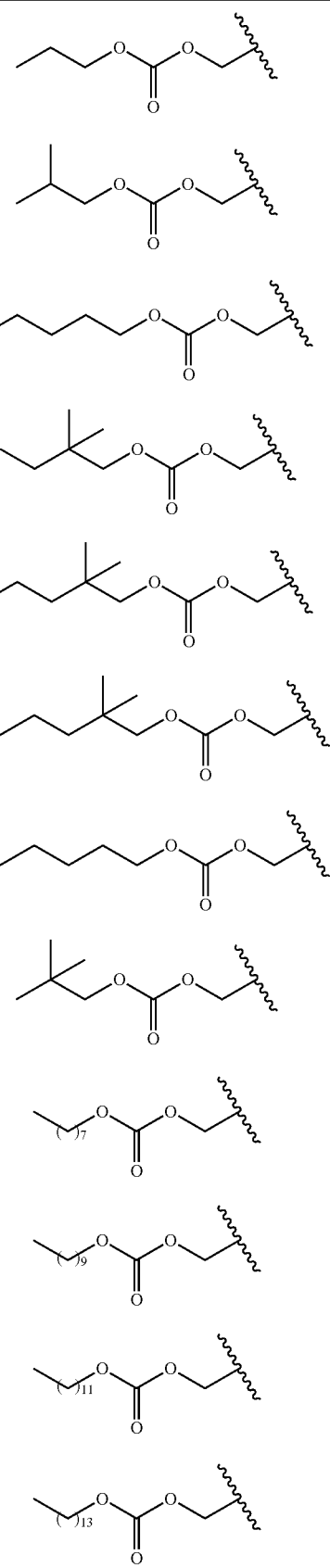
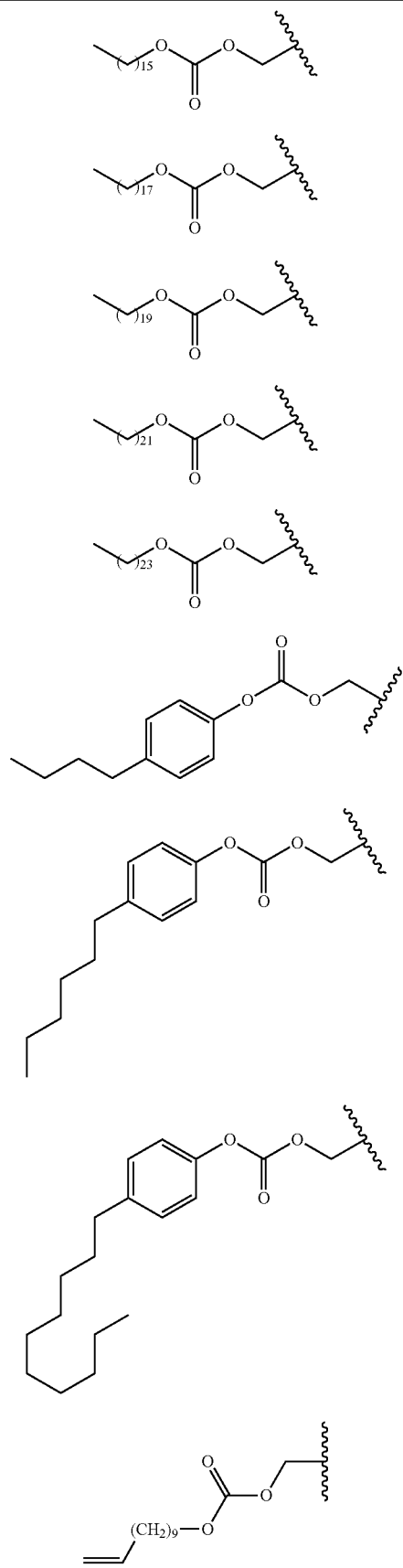

TABLE 4-continued
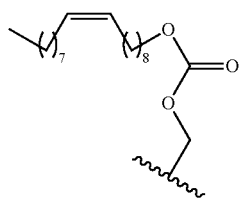
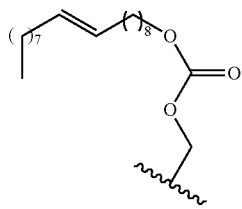
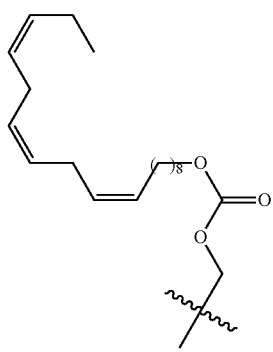
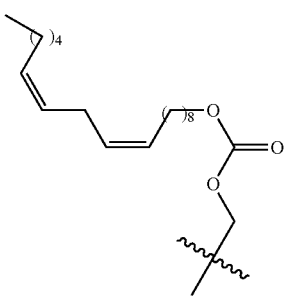
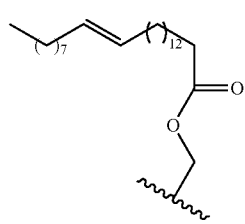
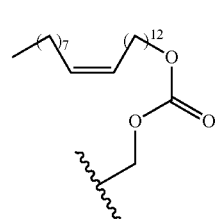
TABLE 4-continued
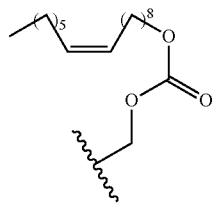
In certain embodiments, variable $R_5$ in any of Formulas I, X, XI, XII, XIII, XIV, XV and XVI is selected from the groups set forth in the Table 5 below.
TABLE 5
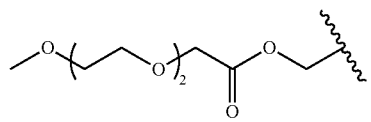
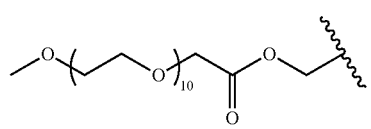
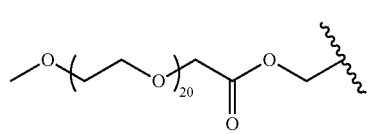
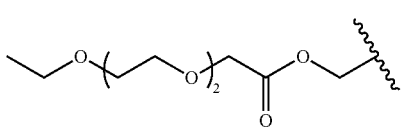
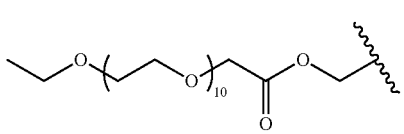
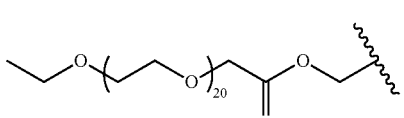
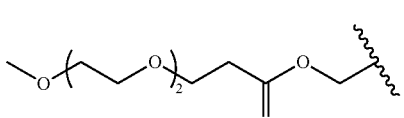
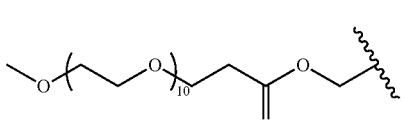
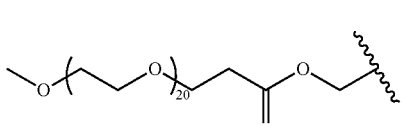

TABLE 5-continued
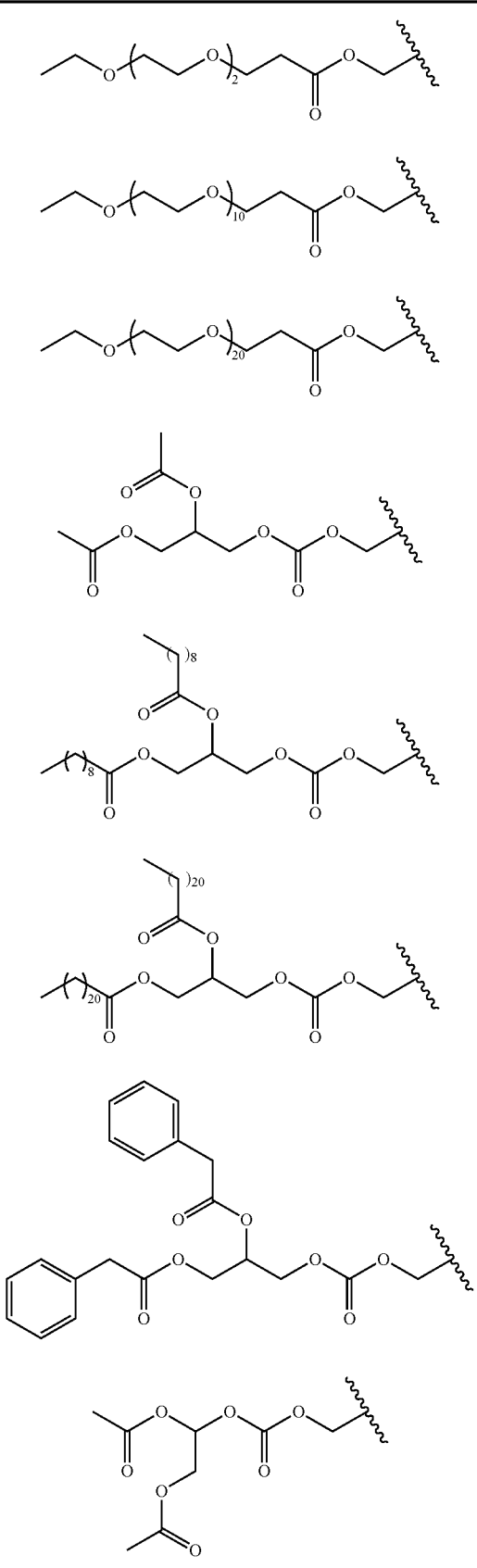
TABLE 5-continued
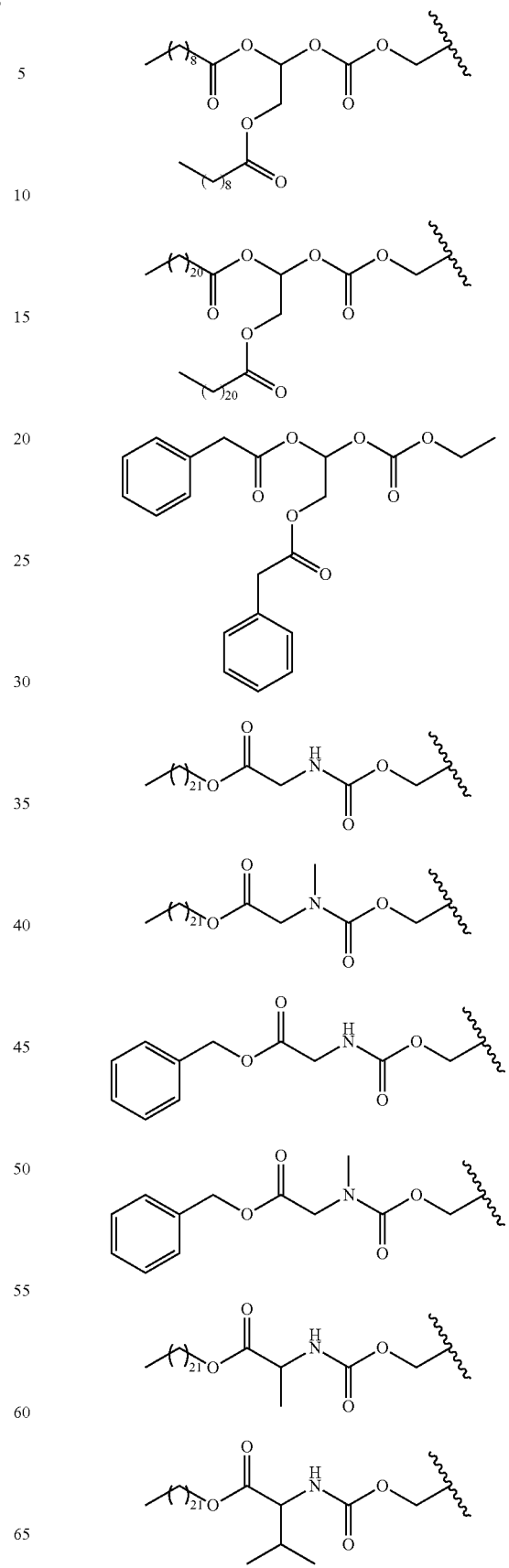

TABLE 5-continued
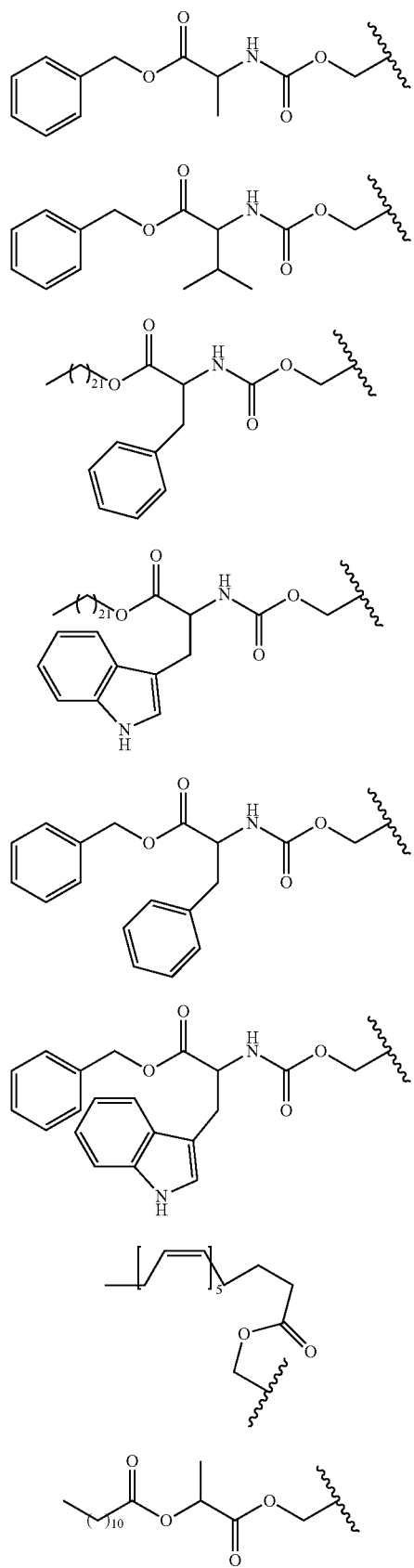
TABLE 5-continued
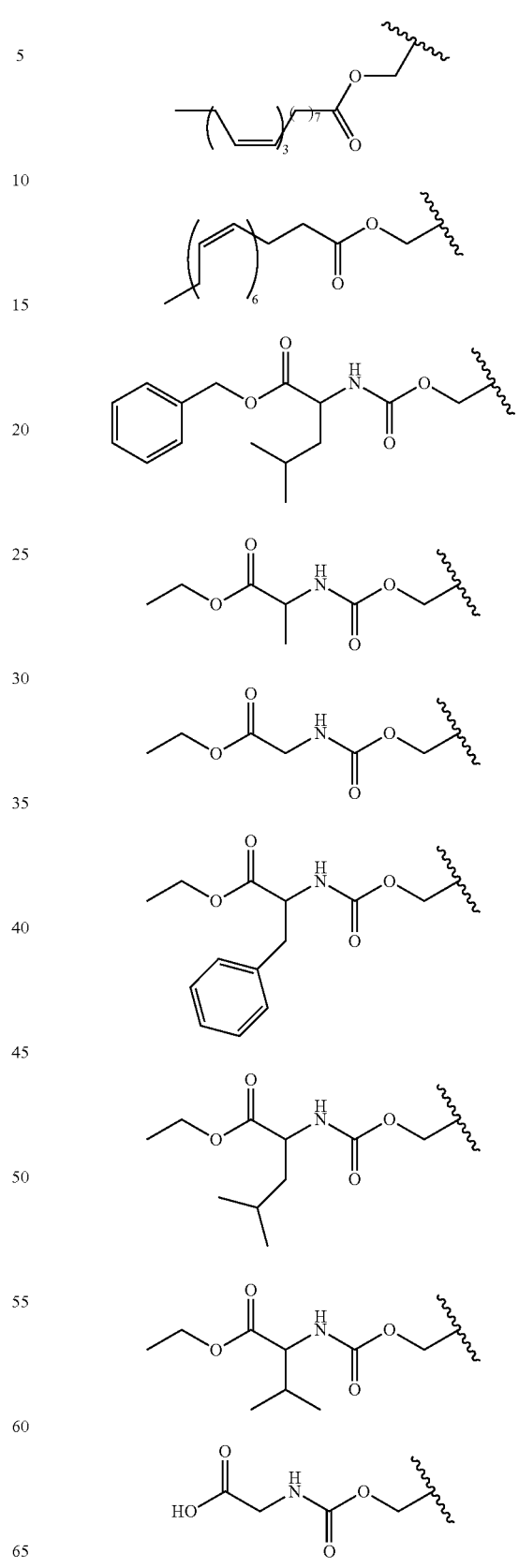

TABLE 5-continued

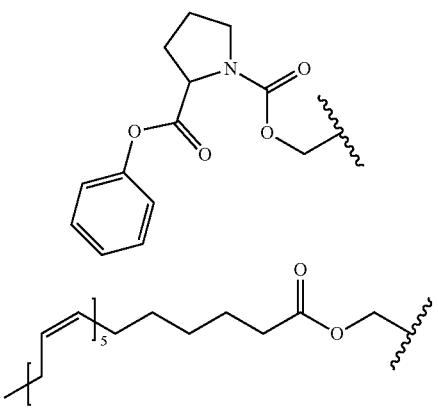

In one embodiment, the invention provides the prodrug compounds represented by the formulas set forth below. The name of the parent drug is presented above each formula. In each of these formulas, $R_5$ can have any of the meanings set forth above, including the identities set forth in Tables 1-5.

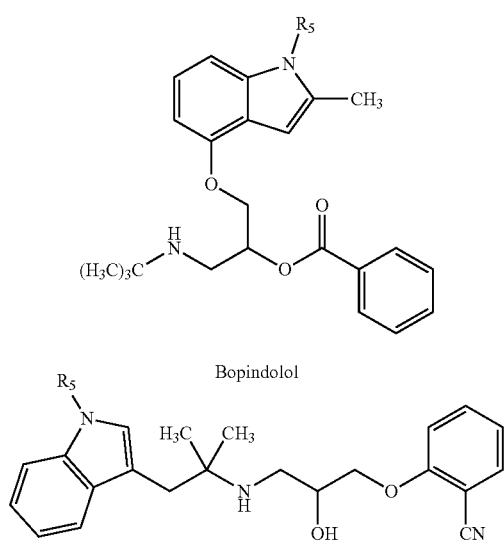

Bopindolol

Bucindolol

Cabergoline

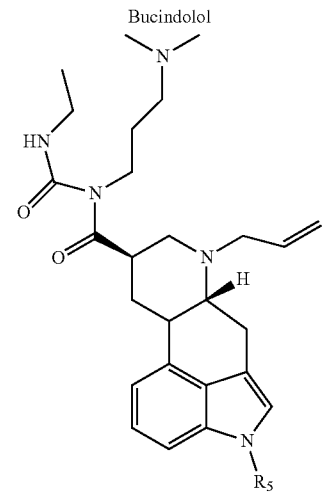

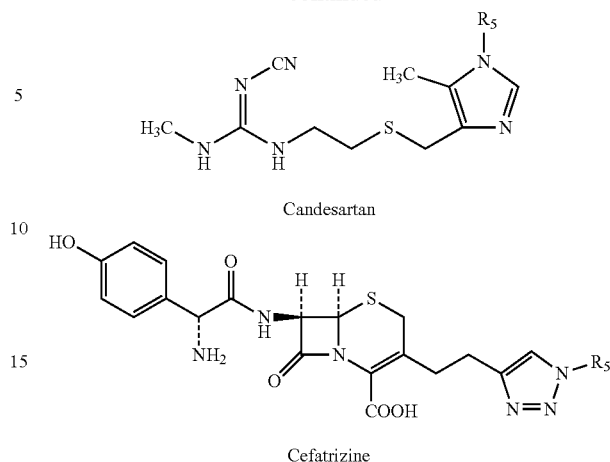

Candesartan

Cefatrizine

Conivaptan

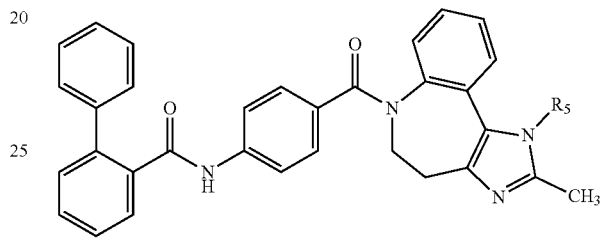

Indoramin

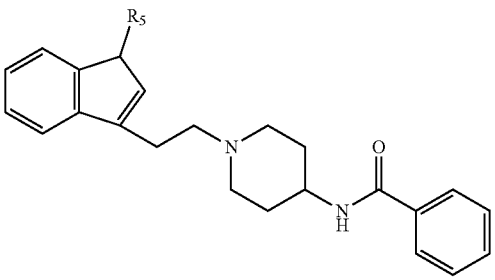

Irbesartan

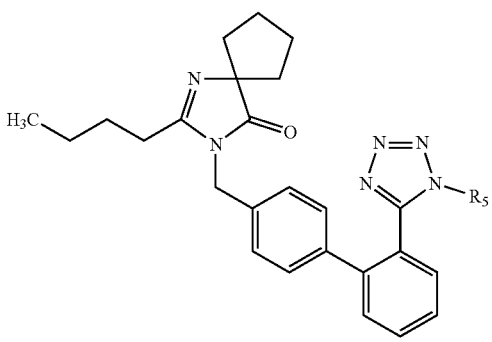

Lansoprazole

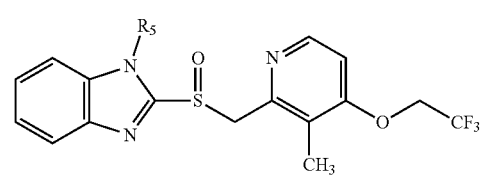

-continued
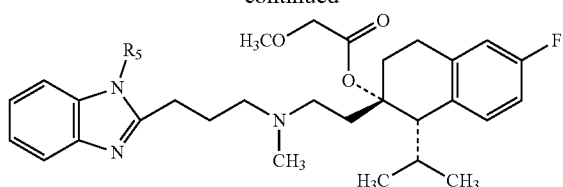
Mibefradil
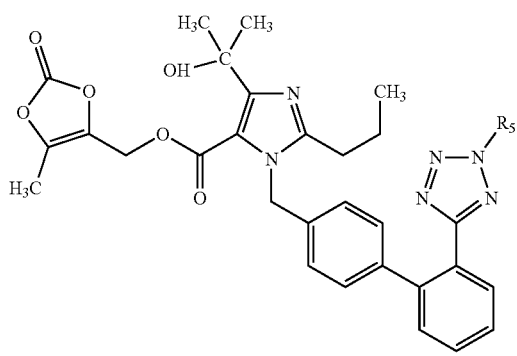
Olmesartan
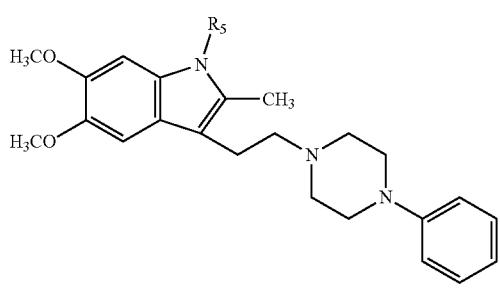
Oxypertine
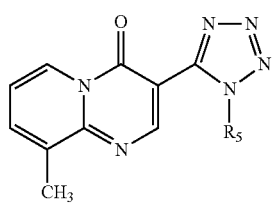
Pemirolast
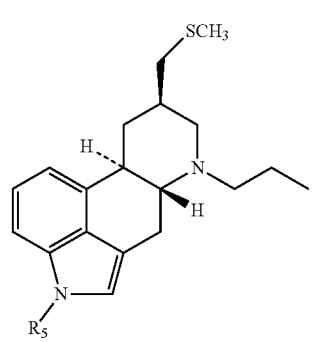
Pergolide
-continued
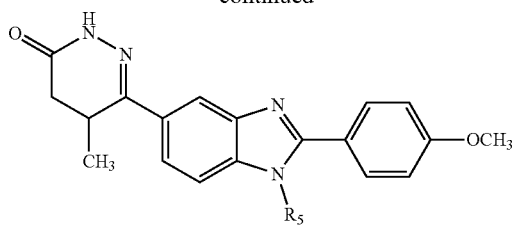
Pimobendan
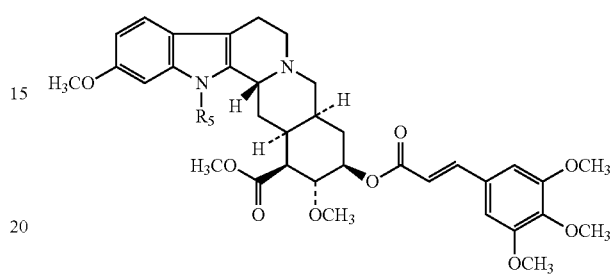
Rescinnamine
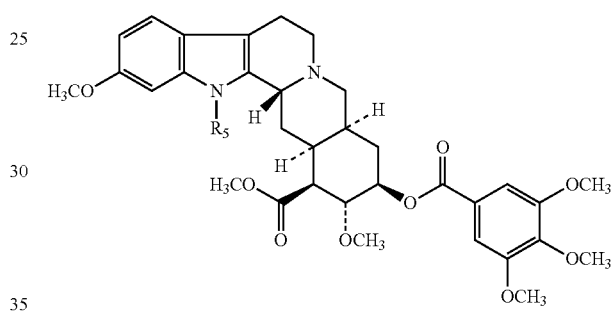
Reserpine
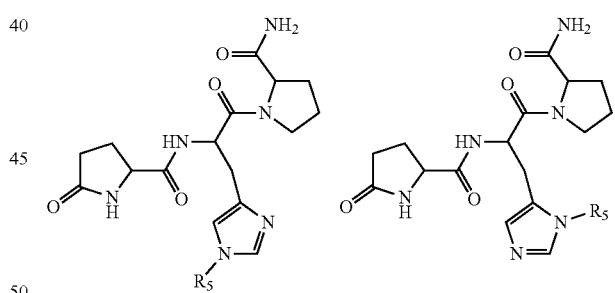
TRH
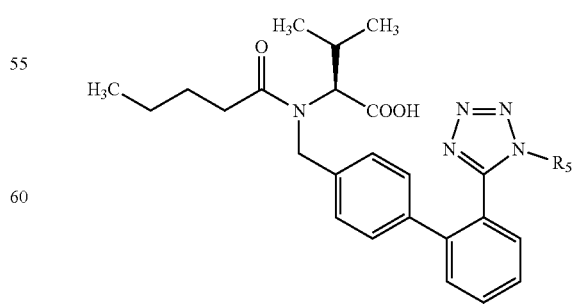
Valsartan -continued

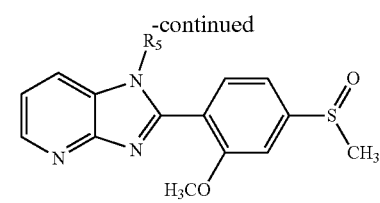
Sulmazole

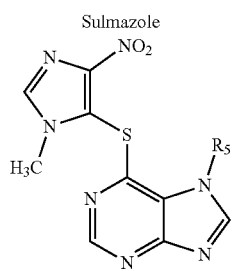
Azathioprine

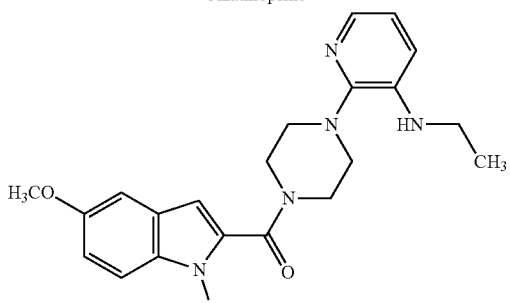
Atevirdine

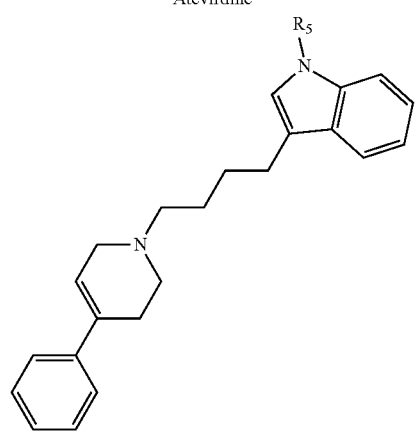
Carmoxirole

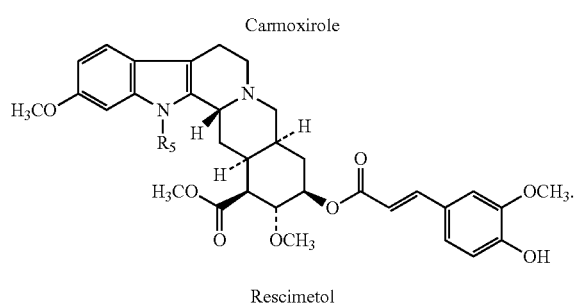
Rescimetol

In a preferred embodiment, a compound of the invention is less soluble at physiological pH in aqueous solvent than the parent drug. In one embodiment, a compound of the invention has a solubility of less than about 0.01 mg/mL, 0.005 mg/mL, 0.001 mg/mL, 0.0005 mg/mL, 0.0001 mg/mL, 0.00005 mg/mL or 0.00001 mg/mL at room temperature in pH 7.4 phosphate buffer. In preferred embodiments, the prodrug has decreased solubility in aqueous solution compared to the parent drug in a pH range from about 1.2 to about 7.5, from about 3 to about 7.5, from about 4 to about 7.5, or from about 5 to about 7.5. In preferred embodiments, the prodrug is at least about 10-fold less soluble than the parent drug at room temperature in pH 7.4 phosphate buffer and/or in one of the foregoing pH ranges.

In a preferred embodiment, a compound of the invention provides sustained delivery of the parent drug over hours, days, weeks or months when administered, for example, orally or parenterally, to a subject. For example, the compounds can provide sustained delivery of the parent drug for up to 1, 7, 15, 30, 60, 75 or 90 days or longer. Without being bound by theory, it is believed that the compounds of the invention form an insoluble depot upon parenteral administration, for example subcutaneous, intramuscular or intraperitoneal injection.

In another embodiment, the invention provides a method for sustained delivery of a parent heteroaromatic NH-containing drug to a subject in need thereof. The method comprises administering to the subject an effective amount of a prodrug formed by substituting the heteroaromatic NH group of the parent with a labile, hydrophobic aldehyde-linked prodrug moiety wherein the prodrug has reduced solubility under physiological conditions compared to the parent drug and provides for longer sustained therapeutic levels of the parent drug following administration than observed levels following administration of the parent drug. In one embodiment, the parent drug is represented by Formula II:

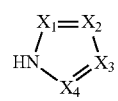

and the prodrug compound is represented by Formula I:

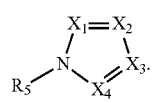

The compounds of the invention can be prepared as acid addition salts. Preferably, the acid is a pharmaceutically acceptable acid. Such acids are described in Stahl, P. H. and Wermuth, C. G. (eds.), *Handbook of Pharmaceutical Salts: Properties, Selection and Use*, Wiley VCH (2008). Pharmaceutically acceptable acids include acetic acid, dichloroacetic acid, adipic acid, alginic acid, L-ascorbic acid, L-aspartic acid, benzenesulfonic acid, 4-acetamidobenzoic acid, benzoic acid, p-bromophenylsulfonic acid; (+)-camphoric acid, (+)-camphor-10-sulfonic acid, capric acid, caproic acid, caprylic acid, carbonic acid, cinnamic acid, cyclamic acid, dodecylsulfuric acid, ethane-1,2-disulfonic acid, ethanesulfonic acid, 2-hydroxyethanesulfonic acid, sulfuric acid, boric acid, citric acid, formic acid, fumaric acid, galactaric acid, gentisic acid, D-glucoheptonic acid, D-gluconic acid, D-glucuronic acid, glutamic acid, glutaric acid, 2-oxoglutaric acid, glycerophosphoric acid, glycolic acid, hippuric acid, hydrochloric acid, hydrobromic acid, hydroiodic acid, isobutyric acid, DL-lactic acid, lactobionic acid, lauric acid, maleic acid, (−)-L-malic acid, malonic acid, DL-mandelic acid, methanesulfonic acid, naphthalene-1,5-disulfonic acid, naphthalene-2-sulfonic acid, 1-hydroxy-2-naphthoic acid, nicotinic acid, nitric acid, oleic acid, orotic acid, oxalic acid, palmitic acid, pamoic acid, phosphoric acid, propionic acid, (−)-L-pyroglutamic acid, salicyclic acid, 4-aminosalicyclic acid, sebacic acid, stearic acid, succininc acid, (+)-L-tartaric acid, thiocyanic acid, p-toluenesulfonic acid, and undecylenic acid.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; cyclodextrins such as alpha-(α), beta-(β) and gamma-(γ) cyclodextrins; starches such as corn starch and potato starch; cellulose and its derivatives such as sodium carboxymethylcellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir. In a preferred embodiment, administration is parenteral administration by injection.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, dimethylacetamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable suspension or emulsion, such as Intralipid®, Liposyn® or Omegaven, or solution, in a nontoxic parenterally acceptable diluent or solvent, for example, as a solution in 1,3-butanediol. Intralipid® is an intravenous fat emulsion containing 10-30% soybean oil, 1-10% egg yolk phospholipids, 1-10% glycerin and water. Liposyn® is also an intravenous fat emulsion containing 2-15% safflower oil, 2-15% soybean oil, 0.5-5% egg phosphatides 1-10% glycerin and water. Omegaven® is an emulsion for infusion containing about 5-25% fish oil, 0.5-10% egg phosphatides, 1-10% glycerin and water. Among the acceptable vehicles and solvents that may be employed are water, Ringer's solution, USP and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

In preferred embodiments, the compounds of the invention, or pharmaceutical compositions comprising one or more compounds of the invention, are administered parenterally, for example, by intramuscular, subcutaneous or intraperitoneal injection. Without being bound by theory, it is believed that upon injection, compounds of the invention form an insoluble or sparingly soluble depot from which prodrug molecules are released over time.

By a "therapeutically effective amount" of a prodrug compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect).

In accordance with the invention, the therapeutically effective amount of a prodrug of the invention is typically based on the target therapeutic amount of the heteroaromatic NH-containing parent drug. Information regarding dosing and frequency of dosing is readily available for many heteroaromatic NH-containing parent drugs, and the target therapeutic amount can be calculated for each prodrug of the invention. In accordance with the invention, the same dose of a prodrug of the invention provides a longer duration of therapeutic effect as compared to the parent drug. Thus if a single dose of the parent drug provides 12 hours of therapeutic effectiveness, a prodrug of that same parent drug in accordance with the invention that provides therapeutic effectiveness for greater than 12 hours will be considered to achieve a "sustained release".

The precise dose of a prodrug of the invention depends upon several factors including the nature and dose of the parent drug and the chemical characteristics of the prodrug moiety linked to the parent drug. Ultimately, the effective dose and dose frequency of a prodrug of the invention will be decided by the attending physician within the scope of sound medical judgment. The specific therapeutically effective dose level and dose frequency for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

Preferred compounds of the invention exhibit sustained activity following dosing compared to dosing with the parent drug. For example, when administered by the same route in the same amount (as measured by equivalents of parent drug), the compounds of the invention provide sustained therapeutic serum levels of parent drug for a significantly longer time than the parent drug. Such administration can be oral, with sustained delivery over hours, or parenteral, with sustained delivery over days, weeks or months.

Dose dumping can create severe consequences for a patient, including permanent harm and even death. Examples of drugs that can be fatal if the therapeutically beneficial dose is exceeded, e.g., by dose dumping, include pain medications such as opioids, as well as other agents active in the central nervous system. In those situations where dose dumping may not be fatal, dose dumping may at least be responsible for side effects, such as increased sedation of the patient as compared to administration of the parent drug alone (not in prodrug form).

The present invention solves the problem of dose dumping and its associated side effects, including but not limited to increased sedation, in a sustained release formulation by providing prodrugs that maintain their reduced solubility and sustained release action in a manner which is independent of the pH of the environment in which the prodrug is administered. During oral administration, the prodrugs of the invention are exposed to a variety of pH conditions including very low pHs in the stomach (e.g. pH 1-2) and then increased pH when crossing the intestinal walls into the bloodstream. During injection it has been observed that the pH at the injection site may also be lowered (e.g. below pH 6.0). CRS 2009 Annual Meeting, Copenhagen Denmark, poster 242; Steen, K. H.; Steen, A. E.; Reeh, P. W. *The Journal of Neuroscience*, (1995), 15: pp. 3982-3989). The pH of an injection site may be lowered for a short amount of time (1-2 hours), but the perturbation may be sufficient to substantially dissolve a basic drug having pH-dependent solubility. In accordance with the invention, the reduced solubility of the prodrugs of the invention remains independent of any change in pH. In one preferred embodiment the reduced solubility of the prodrugs of the invention remains independent over a pH range of pH 4 to pH 8. More preferably the reduced solubility of the prodrugs of the invention remains independent over a pH range of pH 3 to pH 9. Most preferably, the reduced solubility of the prodrugs of the invention remains independent over a pH range of 1.0 to 10.

In addition, it is known that the stability of carboxyl ester linkages, such as those contemplated in the prodrugs of the invention, is dependent on pH with optimum stability occurring at around pH 4-5. If injection site pH fluctuates to a value lower than neutral pH of 7.4, then the stability of the prodrug is increased relative to neutral pH. This stability increase further reduces the risk of early release of active drug from the compound, and thus avoids dose dumping by way of accelerated chemical cleavage of the prodrug.

Definitions

Listed below are definitions of various terms used to describe this invention. These definitions apply to the terms as they are used throughout this specification and claims, unless otherwise limited in specific instances, either individually or as part of a larger group.

The term "aliphatic group" or "aliphatic" refers to a non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as ($C_1$-$C_6$) alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocyclyl, aryl and heteroaryl portion of the acyl group may be substituted as described above in the preferred and more preferred list of substituents, respectively.

The term "alkyl" is intended to include both branched and straight chain, substituted or unsubstituted, saturated aliphatic hydrocarbon radicals/groups having the specified number of carbons. Preferred alkyl groups comprise about 1 to about 24 carbon atoms ("$C_1$-$C_{24}$") preferably about 7 to about 24 carbon atoms ("$C_7$-$C_{24}$"), preferably about 8 to about 24 carbon atoms ("$C_8$-$C_{24}$"), preferably about 9 to about 24 carbon atoms ("$C_9$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$") preferably about 7 to about 24 carbon atoms ("$C_7$-$C_{24}$"), preferably about 8 to about 24 carbon atoms ("$C_8$-$C_{24}$"), and preferably about 9 to about 24 carbon atoms ("$C_9$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$") preferably about 7 to about 24 carbon atoms ("$C_7$-$C_{24}$"), preferably about 8 to about 24 carbon atoms ("$C_8$-$C_{24}$"), and preferably about 9 to about 24 carbon atoms ("$C_9$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$").

The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The terms "heterocyclyl", "heterocycle" "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3- to 6-membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3- to 6-membered heteromonocyclic group containing an oxygen atom, for example, pyranyl, furyl, etc.; unsaturated 3- to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3- to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio" radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The terms "compound" "drug", and "prodrug" as used herein all include pharmaceutically acceptable salts, solvates, hydrates, polymorphs, enantiomers, diastereoisomers, racemates and the like of the compounds, drugs and prodrugs having the formulas as set forth herein.

Substituents indicated as attached through variable points of attachments can be attached to any available position on the ring structure.

As used herein, the term "effective amount of the subject compounds," with respect to the subject method of treatment, refers to an amount of the subject compound which, when delivered as part of desired dose regimen, brings about management of the disease or disorder to clinically acceptable standards.

"Treatment" or "treating" refers to an approach for obtaining beneficial or desired clinical results in a patient. For purposes of this invention, beneficial or desired clinical results include, but are not limited to, one or more of the following: alleviation of symptoms, diminishment of extent of a disease, stabilization (i.e., not worsening) of a state of disease, preventing spread (i.e., metastasis) of disease, preventing occurrence or recurrence of disease, delay or slowing of disease progression, amelioration of the disease state, and remission (whether partial or total).

The term "labile" as used herein refers to the capacity of the prodrug of the invention to undergo enzymatic and/or chemical cleavage in vivo thereby forming the parent drug.

As used herein the term "prodrug" means a compounds as disclosed herein which is a labile derivative compound of a heteroaromatic NH-containing parent drug which when administered to a patient in vivo becomes cleaved by chemical and/or enzymatic hydrolysis thereby forming the parent drug such that a sufficient amount of the compound intended to be delivered to the patient is available for its intended therapeutic use in a sustained release manner.

The term "pharmaceutically acceptable anion" as used herein, refers to the conjugate base of a pharmaceutically acceptable acid. Such anions include acetate, dichloroacetate, adipate, alginate, L-ascorbate, L-aspartate, benzenesulfonate, 4-acetamidobenzoate, benzoate, p-bromophenylsulfonate; (+)-camphorate, (+)-camphor-10-sulfonate, caprate, caproate, caprylate, carbonate, cinnamate, cyclamate, dodecylsulfate, ethane-1,2-disulfonate acid, ethanesulfonate, 2-hydroxyethanesulfonate, sulfate, borate, citrate, formate, fumarate, galactarate, gentisate, D-glucoheptonate, D-gluconate, D-glucuronate, glutamate, glutarate, 2-oxoglutarate, glycerophosphate, glycolate, hippurate, chloride, bromide, iodide, isobutyrate, DL-lactate, lactobionate, laurate, maleate, (−)-L-malate, malonate, DL-mandelate, methanesulfonate, naphthalene-1,5-disulfonate, naphthalene-2-sulfonate, 1-hydroxy-2-naphthoate, nicotinate, nitrate, oleate, orotate, oxalate, palmitate, pamoate, phosphate, propionate, (−)-L-pyroglutamate, salicyclate, 4-aminosalicyclate, sebacate, stearate, succinate, (+)-L-tartrate, thiocyanate, p-toluenesulfonate, and undecylenate. Preferred pharmaceutically acceptable anions include acetate, bromide, camsylate, chloride, formate, fumarate, maleate, mesylate, nitrate, oxalate, phosphate, sulfate, tartrate, thiocyanate and tosylate.

In another embodiment, the invention provides a method of producing a prodrug of a parent heteroaromatic NH-containing drug compound, wherein the prodrug has decreased solubility under physiological conditions and sustained activity upon dosing compared to the parent drug compound. The method comprises modifying the parent drug by substituting a labile, hydrophobic aldehyde-linked prodrug moiety on the heteroaromatic NH nitrogen atom. Preferably, the parent drug compound is represented by Formula II, the prodrug moiety is represented by $R_5$, where $R_5$ has the meaning given above, and the prodrug is represented by Formula I.

Preferably, the step of modifying the parent drug by substituting a labile, hydrophobic aldehyde-linked prodrug moiety on the heteroaromatic NH nitrogen atom comprises reacting the parent drug with an aldehyde in the presence of an acid, such as a carboxylic acid, a carbonic acid, a carbamic acid or a phosphoric acid. The production of prodrugs in this way is illustrated in Scheme 1 below.

Scheme 1

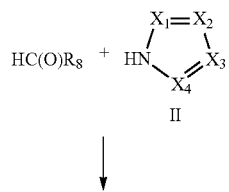

II

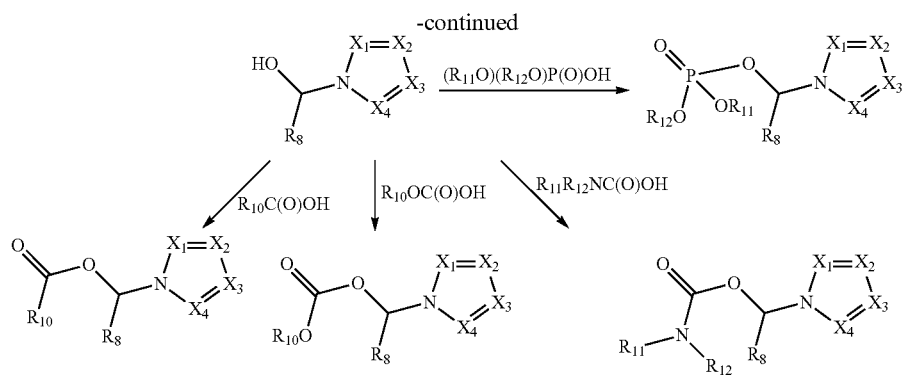

In addition to the reaction of an aldehyde or ketone to compounds of formula VIII, other processes for substitution at the heteroaromatic NH group can be used. For example, alkylation followed by addition of sodium in inert solvents can be used.

An alternative method for preparing prodrug compounds of the invention is illustrated in Scheme 2 below. In this method, the nitrogen atom of the parent drug of formula (II) is alkylated in the presence of base with the alkylating agent $R_5A$, where $R_5$ has the meaning given above and A is a leaving group. Examples of suitable leaving groups include, but are not limited to, tosylate, triflate, p-bromophenylsulfonate, chloride, bromide and iodide.

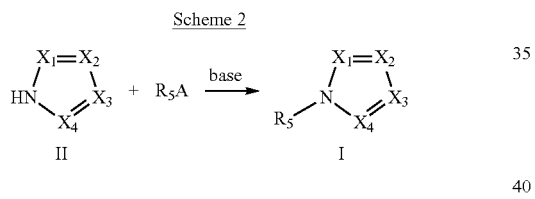

The following non-limiting examples are illustrative of the invention.

EXAMPLES

Example 1

Pemirolast Prodrugs

Prodrugs of pemirolast were prepared using the general procedure set forth below, in which n is 18 (Compound 1), 6 (Compound 2) or 14 (Compound 3).

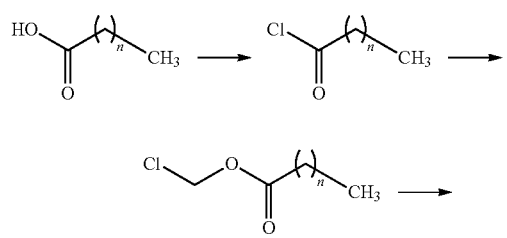

Synthesis of (5-(9-methyl-4-oxo-4H-pyrido[1,2-a]pyrimidin-3-yl)-1H-tetrazol-1-yl)methyl icosanoate (Compound 1)

Synthesis of Arachidoyl Chloride

Oxalyl chloride (2.67 ml, 0.0191 mol) was added dropwise to a mixture of Arachidic acid (6.0 g, 0.0211 mol) and DMF (4 drops) in dichloromethane (50 ml) at 0° C. After the addition was completed, the reaction mixture was stirred at 0° C. for 30 minutes and then stirred at 25° C. for 1 hour, the reaction mixture was partitioned between dichloromethane and water, and the aqueous layer was extracted with dichloromethane. The combined organic extracts were washed with brine, then dried with sodium sulphate and concentrated in vacuo to provide the desired product (6.35 g, 100% yield) as a solid which was not purified any further.

Synthesis of Chloromethyl Arachidate

Arachidoyl chloride (6.35 g, 0.0191 mol) was added drop-wise to a mixture of paraformaldehyde (2.58 g, 0.0191 mol) and anhydrous zinc chloride (0.0523 g, 0.0038 mol) at 0° C. under Argon. After the addition was completed, the reaction mixture was stirred at 25° C. for 1 hour and then heated to 90° C. for 16 hours. The resulting solid was filtered off and washed with dichloromethane. The filtrate was concentrated in vacuo at 37° C. to provide the chloromethyl arachidate (6.7 g, 97% yield). The product was stored over activated molecular sieves (4 Å) and used directly (without purification) in the next step.

Synthesis of Iodomethyl Arachidate

Sodium iodide (8.31 g, 0.0555 mol) was added to a solution of chloromethyl arachidate (6.7 g, 0.0185 mol) in acetonitrile (67 ml) at 25° C. The flask was covered in aluminum foil to protect from light and stirred at 25° C. for 16 hours. The reaction mixture was partitioned between dichloromethane and water. The aqueous layer was extracted with dichloromethane. The combined organic extracts were washed with aqueous saturated $NaHCO_3$, aqueous sodium sulfite (10% solution), and brine, then dried with sodium sulphate and concentrated in vacuo to provide the desired product (5.9 g, 71% yield) as a white solid which was not purified any further.

Synthesis of Compound 1

A 25° C. solution of Pemirolast (1.0 g, 0.0037 mol) in DMF (15 ml) was treated with dry $K_2CO_3$ (1.30 g, 0.0094 mol). After 30 minutes the reaction mixture was treated with iodomethyl arachidate (2.57 g, 0.0056 mol). The reaction mixture was left on stirring for 30 minutes. The reaction mixture was poured into water and extracted with ethyl acetate. The combined organic layer was dried with sodium sulfate and concentrated in vacuo. Flash column chromatography provided the desired product (0.023 g, 1.1% yield).

$^1$H NMR (DMSO, 400 MHz) δ 0.810-0.844 (t, 3H), 1.082-1.208 (m, 32H), 1.261-1.316 (t, 2H), 2.214-2.251 (t, 2H), 2.598 (s, 3H), 6.487 (s, 2H), 7.511-7.546 (t, 1H), 8.112-8.129 (d, 1H), 8.735 (s, 1H), 9.051-9.068 (d, 1H). m/z (M$^+$H) 553.

Synthesis of (5-(9-methyl-4-oxo-4H-pyrido[1,2-a]pyrimidin-3-yl)-1H-tetrazol-1-yl)methyl octanoate (Compound 2)

Synthesis of Chloromethyl Octanoate

Octanoyl chloride (10 g, 0.06 mol) was added drop-wise to a mixture of paraformaldehyde (8.07 g, 0.06 mol) and anhydrous zinc chloride (0.163 g, 0.0012 mol) at 0° C. under Argon. After the addition was completed, the reaction mixture was stirred at 25° C. for 1 hour, and then heated to 90° C. for 16 hours. The solid was filtered off and washed with dichloromethane. The filtrate was concentrated in vacuo at 37° C. to provide the desired product (9.5 g, 84% yield). The product was stored over activated molecular sieves (4 Å), and used directly (without purification) in the next step.

Synthesis of Iodomethyl Octanoate

To a solution of chloromethyl octanoate (9.5 g, 0.0483 mol) in of acetonitrile (100 ml) was treated with sodium iodide (21.7 g, 0.1449 mol). The flask was covered in aluminum foil to protect from light and stirred at 25° C. for 16 hours. The reaction mixture was partitioned between dichloromethane and water, and the aqueous layer was extracted with dichloromethane. The combined organic extracts were washed with aqueous saturated $NaHCO_3$, aqueous sodium sulfite (10% solution), and brine, then dried with sodium sulphate and concentrated in vacuo to provide the desire product (8.4 g, 71% yield) as a yellow oil which was not purified any further.

Synthesis of Compound 2

Dry $K_2CO_3$ (1.30 g, 0.0094 mol) was added to a 25° C. solution of Pemirolast (1.0 g, 0.0037 mol) in DMF (15 ml). After 30 minutes the reaction mixture was treated with iodomethyl octanoate (1.84 g, 0.0056 mol) and then stirred for 30 minutes. The reaction mixture was poured into water and extracted with ethyl acetate. The combined organic layer was dried with sodium sulphate and concentrated in vacuo. Flash column chromatography provided the desired product (0.12 g, 8.2% yield).

$^1$H NMR (DMSO, 400 MHz) δ 0.813-0.856 (t, 3H), 1.119-1.210 (m, 8H), 1.228-1.234 (t, 2H), 1.327-1.363 (t, 2H), 2.239-2.275 (t, 2H), 2.514 (s, 3H), 6.510 (s, 2H), 7.535-7.570 (t, 1H), 8.132-8.156 (d, 1H), 8.759 (s, 1H), 9.072-9.091 (d, 1H). m/z (M$^+$H) 385.

Synthesis of (5-(9-methyl-4-oxo-4H-pyrido[1,2-a]pyrimidin-3-yl)-1H-tetrazol-1-yl)methyl palmitate (Compound 3)

Synthesis of Chloromethyl Palmitate

Palmitoyl chloride (10 g, 0.0363 mol) was added drop-wise to a mixture of paraformaldhyde (4.9 g, 0.0363 mol) and anhydrous zinc chloride (0.99 g, 0.0007 mol) at 0° C. under Argon. After the addition was complete, the reaction mixture was stirred at 25° C. for 1 hour and then heat to 90° C. for 16 hours. The solid was filtered off and washed with dichloromethane. The filtrate was concentrated in vacuo at 37° C. to provide the desired product (9.2 g, 83% yield). The chloromethyl palmitate was stored over activated molecular sieves (4 Å) and used directly (without purification) in the next step.

Synthesis of Iodomethyl Palmitate

A solution of chloromethyl palmitate (9.2 g, 0.0301 mol) in acetonitrile (92 ml) was treated with sodium iodide (13.56 g, 0.0905 mol). The flask was covered in aluminum foil to exclude light and stirred at 25° C. for 16 hours. The reaction mixture was partitioned between dichloromethane and water, and the aqueous layer was extracted with dichloromethane. The combine organics were washed with aqueous saturated $NaHCO_3$, aqueous sodium sulfite (10% solution), and brine, then dried with sodium sulphate and concentrated in vacuo to provide the product (11 g, 91% yield) as a white solid which was not purified any further.

Synthesis of Compound 3

Dry $K_2CO_3$ (2.61 g, 0.0189 mol) was added to a stirred solution of Pemirolast (2.0 g, 0.0075 mol), in DMF (30 ml) at 25° C. After 30 minutes the reaction mixture was treated with iodomethyl octanoate (2.99 g, 0.0075 mol) and stirred for 30 minutes. The reaction mixture was then poured into water and extracted with ethyl acetate. The combined organic layers were dried with sodium sulphate and concentrated in vacuo. Flash column chromatography provided the desired product (0.23 g, 6.2% yield).

$^1$H NMR (DMSO, 400 MHz) δ 0.807-0.841 (t, 3H), 1.063-1.238 (m, 24H), 1.297-1.331 (t, 2H), 2.228 (t, 2H), 2.595 (s, 3H), 6.484 (s, 2H), 7.508-7.544 (t, 1H), 8.108-8.126 (d, 1H), 8.730 (t, 1H), 9.048-9.066 (d, 1H). m/z (M$^+$H) 497.

Example 2

Thyrotropin Releasing Hormone Prodrugs

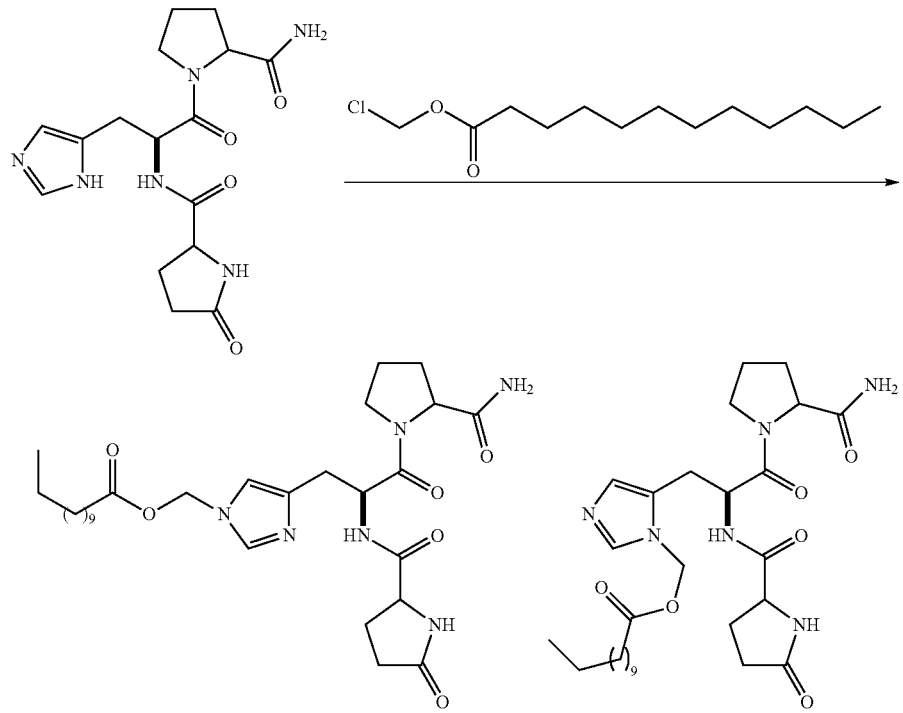

Thyrotropin releasing hormone (0.5 g, 1.38 mmol) was dissolved in N,N-dimethyl formamide (2 mL). Chloromethyl dodecanoate (0.7 g, 2.8 mmol) was then added, and the reaction mixture was stirred at room temperature (20° C.) for 48 hours to provide about 30% conversion to the desired products. The crude reaction mixture was diluted with acetonitrile (4 mL) to form a precipitate. The mixture was filtered and the solid was washed with acetonitrile. The filtrates were purified by preparative HPLC using a Gilson HPLC system (Pump306, Manometer Module 807, Dynamic Mixer 811D, Pump305, Pump306, UV/Vis-151, Eurotherm 5100e), Macherey-Nagel NUCLEODUR 100-30 C18 ec bulk packings and a gradient of A (0.05% TFA in MeCN) and B (0.05% TFA in H2O) (5A to 100A in 50 minutes) at a flow rate of 60 ml/min. The fractions were combined and extracted with ethyl acetate to provide a 1:4 mixture of two isomers of the desired product.

The products of the reaction were subjected to analytical HPLC using a Merck HPLC system (LaChrom, pump type L-6200, UV detector L-7400, interface D6000, HPLC manager D6000). Macherey-Nagel C8-column (Nucleosil 100-5 C8 250/4 mm), with a C18 column (Nucleosil 100-5 C18 250/4 mm), using a gradient of A (0.05% TFA in MeCN) and B (0.05% TFA in H2O) (5A to 100A in 25 minutes) at a flow rate of 1 ml/min. Measured retention times: 16.34 minutes [Isomer 1], retention time 16.88 minutes [Isomer 2]; acetonitrile (0.1% TFA)/H$_2$O (0.1% TFA) system solvent)).

The products of the reaction were analyzed by LC/MS performed on a Agilent 1100 LC/MSD SL Quadrupole Mass Spectrometer. Linear gradients of 5-100% MeCN in H2O/ 0.1% trifluoroacetic acid (1.0 ml/min, T=25 C, WL: 220 nm) on a Nucleosil C18-250:4 100:5 column were used. Both products exhibited MS 575.3 (M+H).

The isomers are believed to result from alkylation of each of the imidazole nitrogen atoms as shown in the scheme above. Major product: $^1$H NMR (CD3OD, 300 MHz) δ 0.90 (t, 3H), 1.22-1.35 (m, 12H), 1.57-1.67 (m, 2H), 1.92-2.07 (m, 4H), 2.22-2.48 (m, 4H), 3.14 (dd, 1H), 3.25 (dd, 1H), 3.50-3.55 (m, 1H), 3.74-3.79 (m, 1H), 4.18-4.22 (m, 1H), 4.44-4.48 (m, 1H), 4.96 (t, 1H), 6.09 (s, 2H), 7.60 (s, 1H), 9.04 (s, 1H).

Example 3

Pharmacokinetic Evaluation of Prodrugs in Rats

Animals: Male Sprague-Dawley rats (Charles River Laboratories, Wilmington, Mass.) are obtained. Approximately 24 rats are used in each study. Rats are approximately 350-375 g at time of arrival. Rats are housed 2 per cage with ad libitum chow and water. Environmental conditions in the housing room: 64-67° F., 30% to 70% relative humidity, and 12:12-h light:dark cycle. All experiments are approved by the institutional animal care and use committee.

Test Compounds: Prodrug compounds of the invention and corresponding parent drugs of the prodrugs tested.

Pharmacokinetics study: Rats are dosed IM by means of a 25 gauge, ⅝ in. needle with 1 cc syringe 0.3 mL suspension is withdrawn from the vial containing the test compound. The rat is injected in the muscles of the hind limb after anesthesia with isoflourane. Blood samples are collected via a lateral tail vein after brief anesthesia with Isoflurane. A 27½G needle and 1 cc syringe without an anticoagulant is used for the blood collection. Approximately 350 μL of whole blood is collected at each sampling time point of 6 hours, 24 hours and 2, 5, 7, 9, 12, 14, 21, 28, 35 days after administration. Once collected, whole blood is immediately transferred to tubes containing K$_2$EDTA, inverted 10-15 times and immediately placed on ice. The tubes are centrifuged for 2 minutes at >14,000 g's (11500 RPMs) using Eppendorf Centrifuge 5417C, F45-30-11 rotor) at room temperature to separate plasma. Plasma samples are transferred to labeled plain tubes (Microtainer®; MFG# BD5962) and stored frozen at <−70° C.

Data Analysis: Drug concentrations in plasma samples are analyzed by liquid chromatography-mass spectroscopy using appropriate parameters for each compound. Half-life, volume of distribution, clearance, maximal concentration, and AUC are calculated by using WinNonlin software, version 5.2.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of sustained delivery to a subject of a compound represented by Formula II,

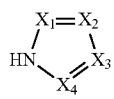

II comprising the step of administering to the subject by intramuscular or subcutaneous infection an effective amount of a compound of Formula I,

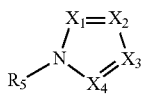

I or a salt thereof, wherein:
each of $X_1$ to $X_4$ is independently N or CR, provided that at least one of $X_1$-$X_4$ is CR;
each R is independently an optionally substituted aliphatic group, an optionally substituted aromatic group or an optionally substituted heteroaromatic group; or any 2 R groups taken together with the carbon atoms to which they are attached form a fused ring;
$R_5$ is selected from —C($R_8$)($R_9$)—O$R_{10}$, —C($R_8$)($R_9$)—OC(O)O$R_{10}$, —C($R_8$)($R_9$)—OC(O)$R_{10}$, —C($R_8$)($R_9$)—OC(O)N$R_{11}R_{12}$, —C($R_8$)($R_9$)—OPO$_3$MY, —C($R_8$)($R_9$)—OP(O)(O$R_{11}$)(O$R_{12}$), —C($R_8$)($R_9$)—OP(O)$_2$(O$R_{11}$)M, —[C($R_8$)($R_9$)O]$_n$—$R_{10}$, —[C($R_8$)($R_9$)O]$_n$—C(O)O$R_{10}$, —[C($R_8$)($R_9$)O]$_n$—C(O)$R_{10}$, —[C($R_8$)($R_9$)O]$_n$—C(O)N$R_{11}R_{12}$, —[C($R_8$)($R_9$)O]$_n$—OPO$_3$MY, —[C($R_8$)($R_9$)O]$_n$—P(O)$_2$(O$R_{11}$)M and —[C($R_8$)($R_9$)O]$_n$—P(O)(O$R_{11}$)(O$R_{12}$);
$R_8$ and $R_9$ are each independently hydrogen, aliphatic or substituted aliphatic;
$R_{10}$ is $C_7$-$C_{24}$-alkyl, substituted $C_7$-$C_{24}$-alkyl, $C_7$-$C_{24}$-alkenyl, substituted $C_7$-$C_{24}$-alkenyl, $C_7$-$C_{24}$-alkynyl, or substituted $C_7$-$C_{24}$-alkynyl;
$R_{11}$ and $R_{12}$ are each independently hydrogen, aliphatic or substituted aliphatic, provided that at least one of $R_{11}$ and $R_{12}$ is $C_7$-$C_{24}$-alkyl, substituted $C_7$-$C_{24}$-alkyl, $C_7$-$C_{24}$-alkenyl, substituted $C_7$-$C_{24}$-alkenyl, $C_7$-$C_{24}$-alkynyl, or substituted $C_7$-$C_{24}$-alkynyl; and Y and M are the same or different and each is a monovalent cation; or M and Y together are a divalent cation; and n is 2 or 3.

2. The method of claim 1, wherein $R_8$ is hydrogen, $C_1$-$C_3$-alkyl, —C(O)H or —CH(OH)CH$_2$OH and $R_9$ is hydrogen.

3. The method of claim 2, wherein $R_8$ is hydrogen.

4. The method of claim 1, wherein $R_5$ is selected from —CH($R_8$)—OC(O)O$R_{10}$, —CH($R_8$)—OC(O)$R_{10}$ and —CH($R_8$)—OC(O)N$R_{11}R_{12}$.

5. The method of claim 1, wherein $R_5$ is selected from —CH($R_8$)—OPO$_3$MY, —CH($R_8$)—OP(O)$_2$(O$R_{11}$)M and —CH($R_8$)—OP(O)(O$R_{11}$)(O$R_{12}$).

6. The method of claim 1, wherein $R_{10}$, or at least one of $R_{11}$ and $R_{12}$, is branched $C_7$-$C_{24}$-alkyl, branched $C_7$-$C_{24}$-alkenyl or branched $C_7$-$C_{24}$-alkynyl.

7. The method of claim 6, wherein $R_{10}$, or at least one of $R_{11}$ and $R_{12}$, is a secondary or tertiary $C_7$-$C_{24}$-alkyl, a secondary or tertiary $C_7$-$C_{24}$-alkenyl or a secondary or tertiary $C_7$-$C_{24}$-alkynyl group.

8. The method of claim 6, wherein $R_{10}$, or at least one of $R_{11}$ and $R_{12}$, is a β-branched $C_7$-$C_{24}$-alkyl, β-branched $C_7$-$C_{24}$-alkenyl or β-branched $C_7$-$C_{24}$-alkynyl group.

9. The method of claim 7, wherein $R_{10}$ is a group represented by one of the formulas below:

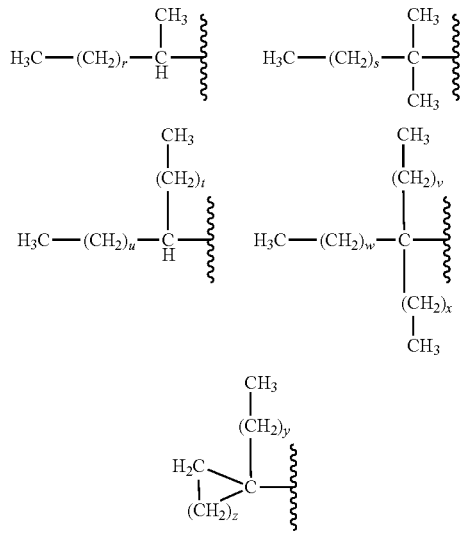

wherein
r is 4 to 21 and s is 3 to 20;
each of t and u is independently 0 to 21, provided that the sum of t and u is from 4 to 21;
each of v, w and x is independently 0 to 20, provided that the sum of v, w and x is from 3 to 20; and
z is an integer from 1 to 10 and y is an integer from 0 to 20, provided that the sum of z and y is from 4 to 21.

10. The method of claim 1, wherein:

(a) the compound of Formula II is represented by the formula:

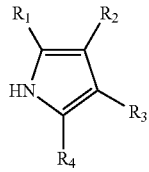

and the compound of Formula I is represented by the formula:

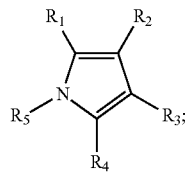

(b) the compound of Formula II is represented by the formula:

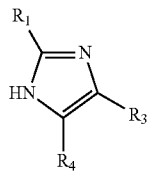

and the compound of Formula I is represented by the formula:

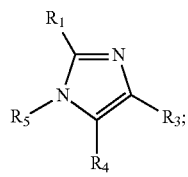

(c) the compound of Formula II is represented by the formula:

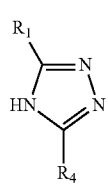

and the compound of Formula I is represented by the formula:

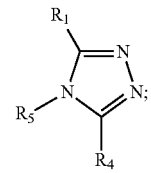

(d) the compound of Formula II is represented by the formula:

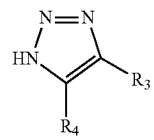

and the compound of Formula I is represented by the formula:

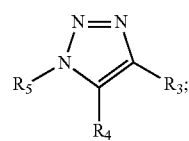

(e) the compound of Formula II is represented by the formula:

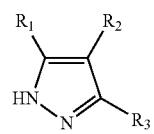

and the compound of Formula I is represented by the formula:

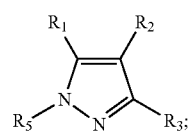

or (f) the compound of Formula II is represented by the formula:

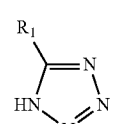

and the compound of Formula I is represented by the formula:

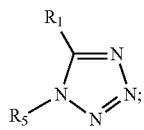

wherein
$R_1$, $R_2$, $R_3$ and $R_4$ are each independently selected from hydrogen, halogen, amino, substituted amino, an optionally substituted aliphatic group, an optionally substituted aryl group and an optionally substituted heterocyclyl group;
or
any two of $R_1$-$R_4$ are taken together with the carbon atoms to which they are attached to form one or more optionally substituted fused ring systems.

11. The method of claim 10, wherein
$R_1$, $R_2$, $R_3$ and $R_4$ are each independently hydrogen, an optionally substituted aliphatic group, an optionally substituted aromatic group, or an optionally substituted heteroaromatic group; or
$R_1$ and $R_2$, $R_2$ and $R_3$, or $R_3$ and $R_4$, together with the carbon atoms to which they are attached, form an optionally substituted cycloalkenyl, aryl, heterocyclyl or heteroaryl ring.

12. The method of claim 1, wherein the compound of Formula II is represented by the formula:

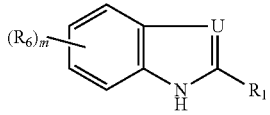

and the compound of Formula I is represented by the formula:

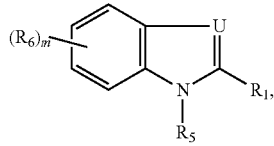

wherein
U is $C(R_2)$ or N;
m is an integer from 0 to 4;
$R_1$ and $R_2$ are each independently selected from hydrogen, halogen, amino, substituted amino, optionally substituted aliphatic, optionally substituted aryl and optionally substituted heterocyclyl;
each $R_6$ is independently optionally substituted aliphatic, aromatic, heteroaromatic or a combination thereof; or
any two of $R_6$, $R_1$ and $R_2$ are taken together with the carbon atoms to which they are attached to form one or more optionally substituted fused ring systems.

13. The method of claim 12, wherein
each $R_6$ is independently selected from hydrogen, halogen, amino, substituted amino, optionally substituted aliphatic, optionally substituted aryl and optionally substituted heterocyclyl; or
two adjacent $R_6$ groups, together with the carbon atoms to which they are attached, form an optionally substituted cycloalkenyl, aryl, heterocyclyl or heteroaryl ring.

14. The method of claim 1, wherein $R_5$ is —$C(R_8)(R_9)$—$OC(O)R_{10}$.

15. The method of claim 14, wherein $R_{10}$ is $C_7$-$C_{24}$-alkyl, $C_7$-$C_{24}$-alkenyl or $C_7$-$C_{24}$ alkynyl.

16. The method of claim 15, wherein $R_8$ and $R_9$ are hydrogen.

* * * * *